US005808012A

United States Patent [19]

Donofrio et al.

[11] Patent Number: 5,808,012

[45] **Date of Patent: *Sep. 15, 1998**

[54] PROTEIN-ENRICHED THERMOPLASTICS

[75] Inventors: David M. Donofrio, Scotts Valley; Erwin R. Stedronsky, San Clemente, both of Calif.

[73] Assignee: Protein Polymer Technologies, Inc., San Diego, Calif.

[ * ] Notice: The term of this patent shall not extend beyond the expiration date of Pat. No. 5,723,588.

[21] Appl. No.: 587,333

[22] Filed: Jan. 16, 1996

Related U.S. Application Data

[63] Continuatin-in-part of PCT/US94/07776, Jul. 8, 1994 which is a continuation-in-part of Ser. No. 89,862, Jul. 9, 1993, Pat. No. 5,723,588.

[51] Int. Cl.[6] ............................ C07K 17/04; C07K 17/08

[52] U.S. Cl. ............................................ 530/815; 525/54.1

[58] Field of Search ............................ 530/815; 525/54.1

[56] References Cited

U.S. PATENT DOCUMENTS 4,617,271 10/1986 Nambu .................................... 435/182

FOREIGN PATENT DOCUMENTS 57-108010 7/1982 Japan .

OTHER PUBLICATIONS

Dale and McBennett, "Stability of High–Temperature Enzymes," ACS Symp. Ser. (1992), 498:136–152.

Finkelstein & Reva, "A Search for the Most Stable Folds of Protein Chains", Nature (1991), 351:497–499.

Goodenough and Jenkins, "Protein Engineering to Change Thermal Stability for Food Enzymes," Biochem. Soc. Trans. (1991), 19:655–662.

Lee and Lee, "Thermal Stability of Proteins in the Presence of Poly(ethylene glycols)," Biochemistry (1987), 26:7813–7819.

MacLeod et al., "Stabilization of Proteins to Heat," Research Disclosure (1984), 244:380.

Matthews et al., "Enhanced Protein Thermostability from Site–directed Mutations that Decrease the Entropy of Unfolding," PNAS USA (1987), 84:6664–6667.

Ponnuswamy et al., "Amino Acid Composition and Thermal Stability of Proteins", Int. J. Biol. Macromol (1982), 4:186–190.

Santoro et al., "Increased Thermal Stability of Proteins in the Presence of Naturally Occurring Osmolytes," Biochemistry (1992), 31:5278–5283.

Wampler et al., "Computational Approaches to Modeling and Analyzing Thermostablity in Proteins," ACS Symp. Ser. (1992), 498:153–173.

Wood and Gadow, "Immobilization of Antibodies and Antigens on macro Solid Phases—A Comparison Between Adsorptive and Covalent Binding", J. Clin.. Chem. Biochem. (1983), 21:789–797.

Wozniak et al., "Crystallographic and Genetic Approaches Toward the Design of Proteins of Enhanced Thermostability," Crystallogr. Model Methods Mol. Des. (1990), Ed. Bugg and Ealick, NY, NY, 80–94.

*Primary Examiner*—Johnny F. Railey, II

*Attorney, Agent, or Firm*—Richard F. Trecartin; Mark T. Kresnak; Flehr Hohbach Test Albritton and Herbert

[57] ABSTRACT

Thermoplastics interdispersed with a variety of functional thermostable proteins and methods for their production are provided. To prepare the subject thermoplastics, a plastic material is contacted with a thermostable polypeptide and then subjected to the heating and molding/extrusion/casting process. The resultant thermoplastics comprise the thermostable polypeptide on the formed plastic surface and at a depth below the plastic surface. The thermostable polypeptides contained in the disclosed compositions retain functional properties or binding specificities through the heating and molding/extrusion/casting processes. Preferred thermostable polypeptides used in the disclosed compositions include silk-like protein polymers, particularly ProNectin®F. The disclosed methods and compositions find use in many applications where plastics containing finctional thermostable proteins are desired, in particular, cell culture-ware.

10 Claims, 1 Drawing Sheet

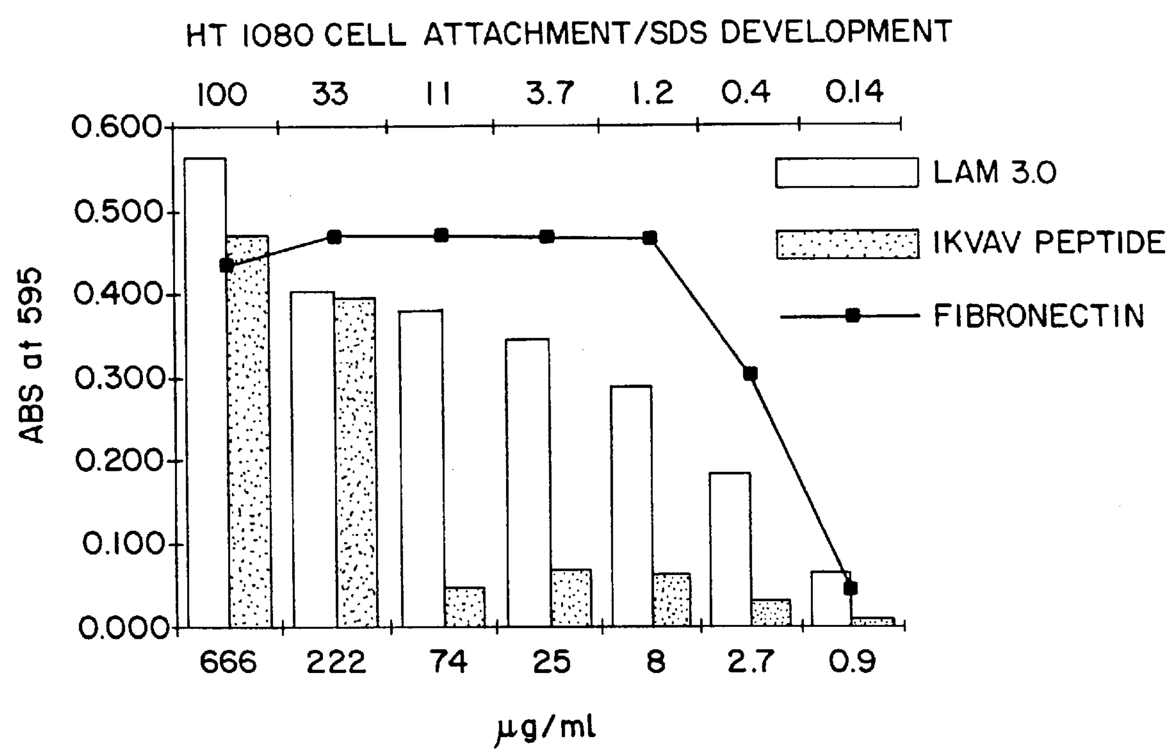
HT 1080 CELL ATTACHMENT/SDS DEVELOPMENT
100
33
11
3.7
1.2
0.4
0.14
0.600
0.500
0.400
0.300
0.200
0.100
0.000
ABS at 595
666
222
74
25
8
2.7
0.9
μg/ml
LAM 3.0
IKVAV PEPTIDE
FIBRONECTIN

PROTEIN-ENRICHED THERMOPLASTICS

CROSS-REFERENCE TO RELATED APPLICATIONS

This application is a continuation-in-part of International application Ser. No. PCT/US94/07776, filed Jul. 8, 1994, which application is a continuation-in-part of application Ser. No. 08/089,862, filed Jul. 9, 1993, now Pat. No. 5, 723,588.

INTRODUCTION

Technical Field

The field of this invention is thermoplastics.

Background

The immobilization of functional polypeptides provides an enormously broad range of applications for medical diagnostics, medical implants, chemical separations, chemical sensors, cultureware, etc. Because of their relatively low reactivity and expense, plastics are the most common solid substrates for protein immobilization. Heat is often used in the fabrication of useful articles from thermoplastic resins and elastomers as well as thermosetting resins and elastomers. Typically the heating and extrusion/molding process requires temperatures in the range of 100°–400° C. or much higher.

Most polypeptides are irreversibly denatured and lose their functional properties at temperatures above about 50°–60° C. The exceptions are polypeptides of a few thermophilic bacteria surviving the environs of hot springs and undersea thermal vents which have recently been shown to have heat stabilities up to 100° C. To accommodate the thermal lability of polypeptide function, immobilization with plastic is accomplished by attaching a selected polypeptide to a pre-formed plastic surface either covalently, usually by chemical activation of the substrate surface, or non-covalently, usually through adsorption.

The vast majority of plastics have hydrophobic surfaces. For many applications such as cell culture and immunodiagnostics, it is critical to have a hydrophilic surface that is wettable by aqueous fluids. Current treatments commercially employed to render the surface hydrophilic include plasma treatment to cause the formation of ionizable chemical groups on the surface, oxidation under conditions of irradiation, or by deposition of surfactants on the surface.

Despite the availability of these methods, there are a number of deficiencies with current polypeptide immobilization methods and compositions. Solvent, vapor or powder deposition methods are labor, time and material intensive. Surface coatings are subject to mechanical wear and erosion, chemical modification or degradation, as well as removal by the action of solvents. Some articles, such as bottles, are difficult to surface coat. Furthermore, especially in the case of cell cultureware, post-manufacture sterilization steps are often required.

Relevant Literature

Wood & Gadow, J. Clin. Chem. Clin. Biochem. (1983) 21: 789–797 review immobilization of proteins on solids; Ponnuswamy et al., Int. J. Biol. Macromol. (1982) 4: 186–190; Dale et al., ACS Symp Ser 498 (1992) (Biocatal. Extreme Temp.) 136–152, Wampler et al., ACS Symp Ser 498 (1992) (Biocatal Extreme Temp) 153–173; Finkelstein & Reva, Nature (1991) 351: 497–499; Goodenough & Jenkins, Biochem. Soc. Trans. (1991) 19: 655–662; Wozniak et al., Crystallogr. Model Methods Mol. Des., (Ed. Bugg and Ealick, NY N.Y.)(1990); Mathews et al., Proc. NatI. Acad. Sci. (1987) 84: 6663–6667 discuss protein compositional parameters relating to thermal stability; Santoro et al, Biochemistry (1992) 31: 5278–5283; Lucy & Lee, Biochemistry (1987) 26: 7813–7819; MacLeod et al, Res. Discl. 244, 380 (1984) describe agents which affect the thermal stability of proteins.

SUMMARY OF THE INVENTION

Thermoplastics comprising functional thermostable polypeptides, as well as methods of making such thermoplastics, are provided. The subject thermoplastics comprise thermostable polypeptides dispersed throughout the plastic matrix, i.e. on the surface and at a depth below the surface. In preparing the subject thermoplastics, a suitable plastic is combined with the thermostable polypeptide and then subjected to conventional heating, molding and extrusion processes. The thermostable polypeptides retain their functional properties throughout the heating, molding and extrusion processes. A variety of functional, thermostable polyptides may be present in the subject thermoplastics, including the silk-like protein polymers, particularly ProNectin®F. The disclosed methods and compositions find use in many applications where plastics containing functional polypeptides are desired, in particular, cell cultureware.

BRIEF DESCRIPTION OF THE DRAWINGS

FIG. 1. is a graph showing HT 1080 Cell Attachment/SDS Development.

DESCRIPTION OF SPECIFIC EMBODIMENTS

Thermoplastics comprising functional thermostable polypeptides, and methods for their production, are provided. In the subject thermoplastics, the functional polypeptide is present throughout the plastic matrix, providing for the presence of polypeptide at both the surface of the plastic as well as at a depth below the surface. The subject thermoplastics present numerous advantages over conventionally coated plastics including: increased durability of the surface activation to mechanical wear and erosion or the action of solvents, increased resistance to chemical modification or degradation, lower costs of production, broader range of articles for manufacture, and the like.

The subject thermoplastics may be prepared from a variety of plastics and thermostable functional polypeptides. Plastics which find use in the subject invention are polymeric materials, preferably organic, of large molecular weight, usually between $10^3$ and $10^6$ MW, which can be shaped and molded by heating and extrusion. In addition to the base plastic or resin, formulations of plastic, including thermosetting polymers, for use in thermomolding applications may include a variety of additives such as stabilizers, accelerators, retardants, antimicrobials, lubricants, fillers, plasticizers, pigments, etc. While is in some instances additives will not be preferred, the compatibility of any selected additive with the methods and compositions disclosed herein can be readily determined.

Preferred plastics are amenable to injection molding (they are melt processable at less than about 300° C. and have Tg's of less than about 200° C.), and are at most minimally reactive, preferably non-reactive, with the thermostable polypeptide to be incorporated therein under injection molding conditions. Plastics of interest include polystyrene, polypropylene, polyethylene, polyvinylchloride, polyvinylidene fluoride, polyvinylidene chloride, acrylonitrile butadiene styrene (ABS), styrene acrylonitrile (SAN), and polyacrylonitrile (PAN). Plastics which find use but also have chemical reactivity toward some protein groups include both aromatic and aliphatic polyamides and polyimides, polyacrylates, polymethacrylate esters, polydioxanone, polyanhydrides, and polyesters such as polycarbonate, polybutylene terphthalate, polyethylene terphthalate, polyglycolic acid and polylactic acid and PLGA copolymers, polyhydroxybutyrate (PHB), polyurethanes, and homopolymers and copolymers of polyvinyl alcohol esters such as polyvinyl acetate and ethylene vinyl acetate. Plastics may also include rubbers such as polysiloxanes, polybutadienes, and neoprenes. However, any plastic capable of thermal extrusion/casting/molding may find use herein.

As numerous applications of the disclosed compositions involve contact with viable biological cells or tissue, biocompatible plastics are especially preferred. Biocompatible plastics are typically non-toxic, biochemically inert, and nonproductive of undesired immune responses when used in vivo. Exemplary biocompatible plastics include polycaprolactone, polycarbonate, polydimethylsiloxane (silicone rubber), polydioxanone, polyether urethane, polyethylene and polyethylene terphthalate, polyglycolic acid and polylactic acid and PLGA copolymers, polyhydroxyethyl methacrylate (HEMA), polymethylmethacrylate (acrylic), and polyvinyl chloride (PVC). Also useful are biodegradable plastics, preferably plastics that degrade under physiological conditions, including polycaprolactone, polydioxanone, polyglycolic acid and polylactic acid and PLGA copolymers, and polyanhydrides. Such plastics are especially useful in diagnostics, therapeutics, and environmental monitoring where time-release of the contained proteins or where subsequent removal of the plastic is inconvenient. Preferred plastics are polystyrene, polypropylene, polyethylene and polyvinyl chloride.

The plastics which are mixed with a thermostable polypeptide according to the present invention may be obtained in any convenient form and are generally commercially available or readily obtained. Generally, a polymerized form is preferred; though, where the polymerization conditions are compatible with the preservation of polypeptide functional integrity, monomers may be used. The compatibility of the polypeptide with the polymerization depends in large part on the reactivity of the particular amino acid composition of the selected protein in the polymerization reaction. For example, vinyl polymerization finds some use while condensation polymerization of polyesters and polyamides is less useful.

The thermostable polypeptides are interdispersed or present on the surface of the plastics as well as being contained within the plastics of the invention. By interdispersed is meant that at least some of the protein is found beneath the surface of the plastic. By incorporating the thermostable protein before or during the thermomolding process rather than as a post-molding coating step, the present invention provides subsurface protein as opposed to solely a surface coating layer on the plastic. Accordingly, the disclosed materials do not have a clearly defined polypeptide-plastic interface. In a preferred embodiment, the thermostable polypeptide is present throughout most of the volume of the thermomolded plastic object. The thermostable polypeptide is present in the range of about 1–10,000 ppm; generally, at less than 2,000 ppm, preferably less than 500 ppm, more preferably less than 100 ppm. The thermostable polypeptide is usually detectable at concentrations greater than 1 ppm, preferably greater than about 10 ppm, at a depth of 0.01 $\mu$m, preferably 0.1 $\mu$m, and more preferably at least about 1 $\mu$m below the surface of the plastic.

By functional thermostable polypeptide is meant a protein, polypeptide, or peptide that at least partially retains the native protein or polypeptide structure (primary, secondary or tertiary) and retains one or more specific functions of the native polypeptide after exposure to the thermal molding/extrusion/casting conditions described herein. Exemplary retained specific functions include catalytic or enzymatic activity, binding specificity, covalent, ionic, or non-covalent interactions with the environment for example, chemical interaction with various reagents, and to a less preferred extent, defined wettability, ionic conductance, etc. By binding specificity is meant a molecular spatial orientation specifically recognizable by, for example, a protein receptor. Examples include cellular ligands (an epitope to which cell surface receptors bind), immunological epitopes (an epitope to which an antibody binds), sugar moieties (an epitope to which a lectin may bind), peptide-specific epitopes (an epitope to which a peptide—usually a synthetic peptide of 3–60 residues screened for component-specific binding from peptide libraries or denovo design—bind), etc.

Functional thermostable polypeptides are readily identified by functional assays of processed plastic containing the polypeptide, commonly cell culture or protein or ligand binding assays, including those used to assess the function of proteins immobilized on surfaces using previous methods in the art, although many other assays may be employed, depending upon the function, which will be readily recognized by those skilled in the art. For example, catalytic activity, binding specificity, physical chemical properties, etc. are all readily tested by conventional immunoassays, spectroscopy, microscopy, etc. Candidate polypeptides for the above functional assays are selected by the potential market of their intended application and predicted functional thermostability. Indications of functional thermostability include resistance to decomposition or irreversible denaturation so as to lose their desired function under the plastic processing conditions; inclusion of relatively few amino acids susceptible to high temperature chemical modification or cleavage such as lysine and aspartic acid; inclusion of relatively high proportions of amino acids known to be associated with thermally stable proteins such as arginine, alanine, threonine, asparagine, isoleucine, or glutamic acid; structures with a high degree of intrachain bonding such as hydrogen bonds or covalent cross-links; hydrogen bonded antiparallel beta sheets with a high accessible surface area; and activity or functionality contained in a single chemically contiguous protein or peptide chain.

The polypeptides are typically of large molecular weight, usually more than about 6 kD, preferably more than 25 kD, more preferably more than 50 kD, and usually below about 200 kD, more usually below about 150 kD. However, polypeptides of at least 3, preferably at least about 6 more preferably at least about 12, most preferably at least about 24 amino acids in length may also be employed. Preferred thermostable polypeptides include structural proteins such as elastin-, collagen-, keratin-, and silk-type proteins, preferably, proteins derived from thermophilic bacteria such as Sulfolobus sulfataricus and Thermus aquaticus (enzymes such as proteases, DNA polymerases, lipases, and metabolic enzymes are especially useful and more preferably, synthetic protein polymers, particularly proteins designed with silk-like protein, SLP blocks (SLPF or FCB-SLPIII (fibronectin)

(ProNectin®F), SLPL (laminin), SLPC (cysteine), SLP3, SLP4, and SELPs (elastin) as described in U.S. patent application Ser. Nos. 609,716 and 114,618, and peptides designed with SLP blocks (peptide 92.7: KKMGAGAGSGAGAGSGAAVTGRGDSPASAAGYGA-GAGSGAGAGS) (SEQ ID NO:01), where ProNectin®F (PnF, SLPF or FCB-SLPIII) is most preferred. The polypeptides may be natural, chemically synthesized, or recombinant proteins, including modified forms such as mutants and fusion products, and also including modifications against thermally induced degradation or denaturation, for example, pegylation.

Genes that encode functional thermostable polypeptides may comprise multimers of DNA sequences encoding the same amino acid sequence unit, where two or more multimers encoding different amino acid units may be joined together to form a block copolymer. The individual units will have from 3–30 amino acids (9–90 nt), more usually 3 or 4 to 25 amino acids (9–75 nt), particularly 3 or 4 to 15 amino acids (9–45 nt), or particularly 3 or 4 to 9 amino acids (9–27 nt), usually having the same amino acid appearing at least twice in the same unit, generally separated by at least one amino acid. The units of the multimer coding for the same amino acid sequence may involve two or more nucleotide sequences, relying on the codon degeneracy to achieve the same amino acid sequence.

Peptide polymers having intervening sequences may provide for chemically active amino acids for chemical crosslink sites, which may serve to covalently attach functional peptides, synthetic or natural polymers or proteins, non-amino acid molecules, and the like. The intervening sequence may be a naturally occurring sequence or a modified naturally occurring sequence. Naturally occurring sequences may be derived from a wide variety of sources with a variety of functions. Such sequences may be a cellular growth inhibitor sequence, e.g. from Tenascin; cell growth promoting attachment factors, e.g. from fibronectin, RGD-, -REDV- (SEQ ID NO:02), laminin B1-YIGSR- (SEQ ID NO:03); bacterial adhesive -SLF-, -ALF-; growth hormones and insulin; inclusion sequences GAGC (SEQ ID NO:04) and GCCV (SEQ ID NO:05), which provide systems for attachment and crosslinking; VSPD(SEQ ID NO:06), VCPD (SEQ ID NO:07) and DPGK (SEQ ID NO:08), which provide an underlining structure.

By thermomolding is meant that the plastic is exposed to heat in the fabrication process. Generally, heat is used to melt the plastic for molding, and, in the present invention, for distributing polypeptide throughout the plastic. Thermomolding refers to any method of heating and forming the plastic and includes extrusion, injection molding, thermoforming, thermosetting, compression molding, etc. Extrusion includes die, cast film, sheet, profile and wire processes. Injection molding is preferred for most articles, especially cultureware, and includes structural foam, blow molding (useful for producing roller bottles), and rotational molding. Less preferred embodiments include reaction injection molding because of potential cross-reactivity with the polypeptide.

Thermomolding is generally performed according to conventional methods. This molding step is usually performed at temperatures in excess of 60° C., preferably in excess of 100° C. and more preferably in excess of 140° C.; though temperatures in excess of 200° C. and 300° C. also find use herein. The manufacturing temperature is determined by the character of the plastic resin as well as the thermostability of the polypeptide. Thermal stability boundaries are readily determined using the methodologies described below. A variety of methods may be employed to enhance the thermal stability of the polypeptides under the thermomolding conditions, such as the addition of organic acids, divalent cations, zwitterions, or saccharides, and decreases in the moisture content of the mixture of polypeptide and plastic prior to thermomolding.

The polypeptide may be added at a variety of stages of the manufacturing process so long as heat is applied during or after the addition of the polypeptide. The polypeptide (in solution or dry) may be mixed with commercial resin pellets before heating and extrusion, with a melt before, in, or after the final metering of the extruder, etc. Dispersing agents may be used to enhance mixing of polypeptides into the plastics under thermomolding conditions. The polypeptide may be added before extrusion and the extruded ribbon reheated while being compressed into the final article. Alternatively, the polypeptide can be applied to the surface of the extruded ribbon and then compression molded to form the final article. For instance, a film can be coated and then heated in a mold to form a microtiter plate.

The thermomolded protein-enriched plastics may take a wide variety of forms depending on the intended application. Preferred forms include sheets, membranes, beads, fibers, hollow fibers, tubes and formed vessels. Preferred vessels include tissue culture matrices such as petri dishes, culture flasks, roller bottles and microtiter-type plates. The plastics may be solid, porous, or semiporous and may be made bio- or environmentally degradable by techniques described herein or otherwise known to those skilled in the relevant art.

The polypeptide-enriched thermoplastics of the present invention find use in a wide variety of applications, including chemical, biotechnology, and health care applications. The materials find use in separation techniques such as chromatographic or filtration matrices; in therapeutic techniques such as controlled drug delivery (e.g. transdermal skin patches and osmotic pumps), sutures, catheters, etc.; in diagnostic techniques; and in tissue culture matrices.

The following examples are offered by way of illustration and not by way of limitation.

EXPERIMENTAL

EXAMPLE 1.

Construction of Silk Like Proteins

Construction of SLP-F9

Two oligonucleotide strands were synthesized and purified as described in the Methods section of the U.S. application Ser. No. 07/609,716 (EP A 89.913054.3).

```
     (PstI)            SnaBI                                              (PstI)
i)   5' - CGCTACGTAGTTCTGCCACGTCCGGTATGTTTCGAAAAAGCTGCA - 3'
ii) 3' - ACGTGCGATGCATCAAGACGGTGCAGGCCATACAAAGCTTTTTCG - 5'
(SEQ ID NOS. 9&10)
```

These oligonucleotide strands were annealed and ligated with plasmid pSY1304 which had been digested with PstI REN.

The product of this ligation reaction was transformed into E. coli strain HB101. Plasmid DNA from transformants was purified and digested with BanI; clones containing inserts of the correct size were digested with BsaAI REN to determine the restriction pattern. Plasmid DNA from correct clones was sequenced. Plasmid pPT0272 (shown in Table 1) contained the desired SLP-F9 monomer sequence.

TABLE 1

| | | | | | | | | | | | | | | | | | |
|---|---|---|---|---|---|---|---|---|---|---|---|---|---|---|---|---|---|
| GGT | GCC | GGC | AGC | GGT | GCA | GGA | GCC | GGT | TCT | GGA | GCT | GGC | GCG | GGC | TCT | GGC | GCG | GGC |
| G | A | G | S | G | A | G | A | G | S | G | A | G | A | G | S | G | A | G |
| GCA | GGA | TCC | GGC | GCA | GGC | GCT | GGT | TCT | GGC | GCA | GGG | GCA | GGC | TCT | GGC | GCA | GGA | GCG |
| A | G | S | G | A | G | A | G | S | G | A | G | A | G | S | G | A | G | A |
| GGG | TCT | GGA | GCT | GCA | CGC | TAC | GTA | GTT | CTG | CCA | CGT | CCG | GTA | TGT | TTC | GAA | AAA | GCT |
| G | S | G | A | A | R | Y | V | V | L | P | R | P | V | C | F | E | K | A |
| GCA | GGC | TAT | GGA | GCT | GGC | GCT | GGC | TCA | GGT | GCT | GGA | GCA | GGA | AGC | GGA | GCG | | |
| A | G | Y | G | A | G | A | G | S | G | A | G | A | G | S | G | A | | |

(SEQ ID NOS:11&12)

Plasmid DNA from pPT0272 was digested with BanI REN and the digestion fragments were separated by agarose gel electrophoresis. The SLP-F9 gene fragment, 222 bp, was excised and purified by NACS column (see Example 1 of U.S. application Ser. No. 07/609,716, EP A 89.913054.3). The purified fragment was ligated with plasmid pSY1262 which had been digested with REN BanI. The product of this ligation reaction was transformed into *E. coli* strain HB 101. Transformants were selected for resistance to kanamycin. Plasmid DNA from individual transformants was purified and analyzed for increased size due to SLP-F9 multiple DNA insertion. Several clones were obtained ranging in size from 1 kbp to 4 kbp. One clone pPT0275, with an insert of approximately 2.7 kbp was chosen for expression and protein analysis.

SLP-F9 Expression

An overnight culture which had been grown at 30° C. was used to inoculate 50 ml of media contained in a 250 ml flask. Kanamycin was added at a final concentration of 50 $\mu$g per ml and the culture was incubated with agitation (200 rpm) at 30° C. When the culture reached an $OD_{600}$ of 0.8, 40 ml were transferred to a new flask prewarmed at 42° C. and incubated at the same temperature for approximately 2 hours. The cultures (30° and 42°) were chilled on ice and $OD_{600}$ was taken. Cells were collected by centrifugation divided in 1.0 $OD_{600}$ aliquot and used to perform dot blot and western analysis using SLP antibodies. For purification and amino acids analysis larger cultures were used.

pPT0275 SLP-F9 945 AA 75,561 MW (SEQ ID NO:13)

MDPVVLQRRDWENPGVTQLNRLAAHPPFASDPMGAGS $(GAGAGS)_6$ $[GAARYVVLPRPVCFEKAAGY\ (GAGAGS)_9]_{11}$

GAARYVVLPRPVCFEKAAGY $(GAGAGS)_2$ GAGAMDPGRYQLSAGRYHYQLVWCQK

Construction of SLP-L3.0

An additional two oligonucleotide strands were synthesized as described in the Methods section of U.S. application Ser. No. 07/609,716 (EP A 89.913054.3).

```
         (PstI)            ClaI                                        (PstI)
iii)     5' - CCGGGTGCATCGATCAAAGTAGCTGTTAGCGCCGGACCGTCTGCA - 3'
 iv) 3' - ACGTGGCCCACGTAGCTAGTTTCATCGACAATCGCGGCCTGGCAG - 5'
(SEQ ID NOS. 14 & 15)
```

These oligonucleotide strands were annealed and ligated with plasmid pSY1304 which had been digested with PstI REN.

The product of this ligation reaction was transformed into *E. coli* strain HB 101. Plasmid DNA from transformants was purified and digested with BanI; clones containing inserts of the correct size were digested with StuI and ClaI RENs to determine the restriction pattern. Plasmid DNA from correct clones was sequenced. Plasmid pPT0271 (shown in Table 2) contained the desired SLP-L3.0 monomer sequence.

TABLE 2

| | | | | | | | | | | | | | | | | | | |
|---|---|---|---|---|---|---|---|---|---|---|---|---|---|---|---|---|---|---|
| GGT | GCC | GGC | AGC | GGT | GCA | GGA | GCC | GGT | TCT | GGA | GCT | GGC | GCG | GGC | TCT | GGC | GCG | GGC |
| G | A | G | S | G | A | G | A | G | S | G | A | G | A | G | S | G | A | G |
| GCA | GGA | TCC | GGC | GCA | GGC | GCT | GGT | TCT | GGC | GCA | GGG | GCA | GGC | TCT | GGC | GCA | GGA | GCG |
| A | G | S | G | A | G | A | G | S | G | A | G | A | G | S | G | A | G | A |
| GGG | TCT | GGA | GCT | GCA | CCG | GGT | GCA | TCG | ATC | AAA | GTA | GCT | GTT | AGC | GCC | GGA | CCG | TCT |
| G | S | G | A | A | P | G | A | S | I | K | V | A | V | S | A | G | P | S |
| GCA | GGC | TAT | GGA | GCT | GGC | GCT | GGC | TCA | GGT | GCT | GGA | GCA | GGA | AGC | GGA | GCG | GGT | GCC |
| A | G | Y | G | A | G | A | G | S | G | A | G | A | G | S | G | A | G | A |

(SEQ ID NOS: 16&17)

Plasmid DNA from pPT0272 was digested with BanI REN and the digestion fragments were separated by agarose gel electrophoresis. The SLP-L3.0 gene fragment, 222 bp, was excised and purified by NACS column (see Example 1 of U.S. application Ser. No. 07/609,716). The purified fragment was ligated with plasmid pSY1262 which had been digested with REN BanI. The product of ligation reaction was transformed into *E. coli* strain HB101. Transformants were selected for resistance to kanamycin. Plasmid DNA from individual transformants was purified and analyzed for increased size due to SLP-L3.0 multiple DNA insertion. Several clones were obtained ranging in size from 1 kbp to 4 kbp. One clone pPT0278, with an insert of approximately 2.9 kbp was chosen for expression and protein analysis.

SLP-L3.0 Expression

An overnight culture which had been grown at 30° C. was used to inoculate 50 ml of media contained in a 250 ml flask. Kanamycin was added at a final concentration of 50 μg per ml and the culture was incubated with agitation (200 rpm) at 30° C. When the culture reached an $OD_{600}$ of 0.8, 40 ml were transferred to a new flask prewarmed at 42° C. and incubated at the same temperature for approximately 2 hours. The cultures (30° and 42°) were chilled on ice and $OD_{600}$ was taken. Cells were collected by centrifugation divided in 1.0 $OD_{600}$ aliquot and used to perform dot blot and western analysis using SLP antibodies. For purification and amino acids analysis larger cultures were used.

pPT0278 SLP-L3.0 1019 AA 75,639 MW (SEQ ID NO:18)
MDPVVLQRRDWENPGVTQLNRLAAHPPFASDPMGAGS (GAGAGS)$_6$
[GAAPGASIKVAVSAGPSAGY (GAGAGS)$_9$]$_{12}$
GAAPGASIKVAVSAGPSAGY (GAGAGS)$_2$ GAGAMDPGRYQLSAGRYHYQLVWCOK

Activity of SLP-L3.0

SLP-L3.0 was purified from *E coli* strain pPT0278 using standard extraction and protein separation techniques. Purity of the final product was determined by amino acid compositional analysis and microchemical elemental analysis to be 94.6% by weight.

SLP-L3.0 was evaluated for its ability to promote the attachment of a fibrosarcoma cell line, HT1080, commonly used for attachment assays on collagen, fibronectin and laminin. The purified product was dissolved in a solution of 4.5 M $LiClO_4$ and diluted in phosphate buffered saline (PBS) to concentrations ranging from 100 to 0.14 μg/ml. 0.1 ml of the diluted polymer solution was dispensed to individual wells of a tissue culture polystyrene multi-well dish. The solution was left in contact with the surface of the dish for 2 hours then the dish was rinsed with PBS several times and incubated with freshly harvested HT1080 cells in serum-free medium. After one hour, unattached cells were removed by rinsing in PBS and attached cells were fixed and stained with a blue dye. The stained cells were quantified by solubilizing the dye and determining its solution absorbance by spectrometry at a wavelength of 595 nm.

The attachment experiment was run in parallel with wells coated with fibronectin and a synthetic peptide of the sequence RKQAASIKVAVS (SEQ ID NO:19). FIG. 1 shows a titration curve for cell attachment as a function of coating concentration. The results indicate that SLP-L3.0 (shown as LAM 3.0) promotes the attachment of HT1080 cells to tissue culture polystyrene coated with the polymer in a dose dependent manner. Maximum activity is observed at the greatest coating concentration used in this experiment, 100 μg/ml. Although the activity drops with coating concentration, cell attachment is observed greater than background even at the lowest concentration, 0.14 μg/ml. The polymer has significantly greater activity than the laminin peptide at concentrations of 74 μg/ml or less. Considering the difference in molecular weight between the polymer and the synthetic peptide, the polymer has 32 times greater activity than the peptide on the basis of number of active sequences. The polymer compares favorably with the attachment activity of fibronectin, even though different binding receptors would be utilized in each case.

In order to evaluate the polymer's ability to stimulate neurite outgrowth, PC12 cells were grown on plastic dishes coated with polylysine, collagen type I, fibronectin, the peptide RKQAASIKVAVS (SEQ ID NO:19), SLP-L3.0, and laminin. The cells were stimulated with nerve growth factor to undergo neural differentiation. The number and lengths of neural cell processes that extended from these cells were observed. SLP-L3.0 did promote neural outgrowth of PC12 cells to a significantly greater degree than uncoated dishes. The activity of SLP-L3.0 was greater than all of the substrates except laminin.

EXAMPLE 2.

Thermoplastics Comprising Thermostable Polypeptides

Extrusion of polystyrene coated with ProNectin®F

Crystalline polystyrene (PS) pellets (454 grams) were washed with isopropyl alcohol (500 ml per wash) three times to remove surface contaminants and then air dried. The pellets were rinsed in 800 mls of phosphate buffered saline (PBS). A solution containing 200 mg of ProNectin®F (SLPF batch RX4, Protein Polymer Technologies, Inc.) dissolved in 20 mls of 4.5M lithium perchlorate was diluted by adding 780 ml of PBS to yield a final ProNectin®F concentration of 0.25 mg/ml. The solution was then added to the pellets and stirred gently overnight for maximum adsorption of the ProNectin®F on the polystyrene surface. The pellets were then rinsed three times with deionized water then air dried.

The amount of ProNectin®F adsorbed to the surface of the polystyrene pellets was measured by amino acid analysis. 253 mg of coated pellets were placed in a sealed glass hydrolysis vial containing 100 $\mu$l of 0.1N HCl and flushed with nitrogen gas. The vial was incubated at 100° C. for 24 hrs. The liquid contained in the vial was removed and the pellets rinsed with 150 $\mu$l of 0.1N HCl. The hydrolysis solution and the rinse were combined in a tube and dried under vacuum. The amino acid residues contained in the tube were derivatized by addition of isophenylthiocyanate according to standard protocols. The derivatized amino acids were separated by HPLC reverse phase chromatography, detected spectroscopically and quantified based on their adsorption as compared to known standards. The pellet hydrolysis was shown to contain 6.6 $\mu$g of amino acids per 253 mg of coated polystyrene or 26.1 $\mu$g of amino acids/g polystyrene. The dimensions of an average pellet were measured and the surface area was calculated to be approximately 0.3 $cm^2$/13 mg or 23 $cm^2$/g. Therefore, the coated pellets contained on average 26.1 $\mu$g of amino acids/23 $cm^2$ of polystyrene or 1.1 $\mu g/cm^2$. That ProNectin®F was the only source of the amino acids on the coated pellets is evidenced by the fact that the amino acid content of the polystyrene hydrolysate closely matched the amino acid content of the ProNectin®F batch used in the coating. Accordingly, this procedure deposited approximately 1.1 $\mu$g of ProNectin®F per $cm^2$ of polystyrene surface area.

The dried ProNectin®F-coated pellets were fed into a heated single screw extruder fitted with a 2"×⅛" ribbon die. Temperature was controlled in the extruder barrel to maintain the polystyrene melt temperature at 390° Fahrenheit. A first extrusion was made on a moving belt to produce a continuous ribbon. The ribbon was allowed to cool and then cut into 2"×2" pieces. A second extrusion was conducted whereby the continuous ribbon was passed to a Carver press fitted with heated platens and compressed to 1/16" thickness. The cooled ribbon was then cut into 2"×2" pieces.

Cut pieces of both the raw extruded and compression molded polystyrene ribbon were placed in 100 mm diameter polystyrene petri dishes. Delbecco's Modified Eagles Medium (DMEM) (25 ml) was added to the dishes to cover the cut pieces. Medium was also placed in empty polystyrene petri dishes to serve as negative controls. A suspension (25 ml) of viable African Green Monkey Kidney (VERO) cells at $4\times10^5$ were pipetted into all petri dishes and allowed to settle on the cut pieces or empty dish bottom. The petri dishes were then incubated for 1.5 hrs at 37° C. in a 5% $CO_2$ atmosphere to allow cell attachment. The cut pieces and empty dishes were washed twice with PBS to remove unattached cells then 3% formaldehyde solution was added to fix attached cells by standing at room temperature for 5 min. The fixed cells were stained by adding 0.01% amido black in 40% methanol and 10% acetic acid solution. After 10 min staining the cut pieces and empty dishes were destained in 90% methanol, 8% acetic acid, 2% water. Attached cells were observed microscopically and photographed.

Both the raw extruded and compression molded polystyrene pieces showed considerable darkening on their surface indicating adsorption of the amido black stain by attached cells, whereas the empty polystyrene dishes showed no color development on the dish bottom indicating the lack of attached cells. Microscopic observation confirmed that the raw extruded and compression molded polystyrene surfaces were covered with attached cells, whereas the empty polystyrene dishes showed no color development on the dish bottom indicating the lack of attached cells.

The presence of attached cells on the extruded polystyrene and lack of attached cells on the empty dishes substantiates that the functionality of ProNectin®F as a cell attachment ligand was maintained through the extrusion process.

Non-Washed Powdered Polystyrene

A mixture of solid dry ice for cooling and polystyrene pellets without added zinc stearate, lubricants, or waxes (Amoco IR3 -C0) was ground to a powder without added suspending liquid using a standard laboratory Waring blender. The polystyrene powders were sized using American Standard stainless steel sieves. Polystyrene powder of>100 mesh was taken for these experiments. No attempt was made to wash the polystyrene after the grinding operation. ProNectin®F (4 mg) was dissolved in 30 ml of 85% formic acid, slurried with 10 g of the sieved polystyrene powder, and concentrated to dryness on the rotary evaporator using bath temperatures of less than 60° C.

Several sample films from each lot of powder were compression molded using the standard protocol as follows. 250 mg of coated polystyrene powder were compression molded between 304 stainless steel plattens using a Carver press with plattens heated electrically to 150° C. and a maximum force of 1500 Kg for 5–10 seconds. Disks of 7 mm diameter were punched out of the films and were placed in individual wells of a 96 well tissue culture plate. The cell attachment assay was conducted as described above. Film samples were assayed in quadruplicate. The goal of this set of experiments was to explore methods of washing the films after they were installed into the tissue culture plate. Combinations of isopropanol, 1 mM aqueous EDTA, and 1% (w/v) Triton X-100 were used for these washes. A few disks in two lanes showed positive cell attachment signals. No obvious correlation with processing protocols could be established from these experiments.

Attachment Assay Using VERO Cells

The silicone grease "adhesive" used to affix compression molded test disks to the tissue culture plates was prepared by diluting Dow Corning High Vacuum Grease with cyclohexane to a final concentration of 25% w/v, centrifuging to compact the silica filler, and retaining the supernatant. To each well of a 96-well tissue culture plate which is to receive a test disk was added 25 $\mu$l of the silicone adhesive solution. The plate was then dried overnight in a vacuum oven at 40° C. In all operations, best results were obtained when all wash and aspiration steps were performed using a Biotek 403H automated plate washer with settings: dispense height=10; plate height=100; dispense volume=200 $\mu$l; and number of washes=2.

One lane of the plate, as a positive control, was solution coated with ProNectin®F. A stock solution of ProNectinq®F (1 mg/ml) was prepared in 4.5M aqueous lithium perchlorate. This stock solution (10 $\mu$l) was diluted into 10 ml of 1× calcium-magnesium free phosphate buffered saline (cmf PBS) to yield a coating solution with a final concentration of 1 μg/ml. Coating solution (100 μl) was added to each well which is to serve as a positive control and incubated at room ambient temperature for 1.5 hours.

While the positive control lane was being solution coating with ProNectin®F, the 7 mm diameter test disks were placed into 5 dram vials and washed 3 times with 5 ml of 1× cmf PBS. The test disks were then placed into each well and gently pressed into the silicone grease which had been layered on the bottom of the well. After mounting the test disks into the plate, they were washed twice with 200 μl of 1× cmf PBS. At this time, the background absorbances were read using a Titertek Plate Reader at 595 nm. Blocking solution (2 mg of bovine serum albumin per milliliter of cmf PBS), 100 μl, was added to each well and incubated for 2 hours at room ambient temperature and one hour at 37° C. The blocking solution was aspirated and the plate rinsed once with 1× cmf PBS.

VERO cells, $2\times10^5$ cells from a suspension prepared at $2\times10^5$ cells/ ml, were added to each well using DME culture media without fetal bovine serum and the plate incubated for 1 hour in 5% carbon dioxide at 37° C. The media containing the cells was aspirated and the plate rinsed twice with 200 μl 1× cmf PBS. Fixative solution (3.7% formaldehyde in 1× cmf PBS), 100 μl, was added to each well and incubated for 5–10 minutes at room ambient temperature. The fixative solution was aspirated. Staining solution (0.1% amido black in 40% methanol-10% acetic acid), 100 μl, was added, and the plate was incubated for 30–60 minutes at room ambient temperature. The plate was then aspirated and rinsed with deionized water to remove all soluble dye. Absorbances were read using a Titertek Plate Reader at 595 nm.

Effects of Additives In the Polystyrene

Experiments were conducted using polystyrene pellets from a lot without added zinc stearate, mineral oil, or wax. The native pellets were reduced to a powder by dry grinding in a coffee grinder. The recovered powder was washed with isopropanol on a Buchner funnel, air dried, and sieved to various mesh sizes. The ProNectin®F was deposited onto the polystyrene powder of 60–80 mesh using a modified vortex dilution technique. The polymer powders (5.0 g) were slurried in 15 ml of water. While vortexing, a solution of ProNectin®F in formic acid (1 mg/15 ml) was added in one portion. While vortexing, water (30 ml) was added over about 60 seconds.

Several sample films from each lot of powder were compression molded and cell attachment assays were conducted on a single 96-well plate according to our standard protocols described above. (See Attachment Assay Using VERO Cells).

In the above table, the polystyrene sample [Amoco IR3-C0] has no added zinc stearate or added waxes, while the polystyrene sample [Amoco GR3-C7] has 1700 ppm zinc stearate and added waxes.

After the disks were mounted on the tissue culture plate with silicone grease, a matrix of optical densities were measured according to our standard protocol as follows. The optical densities reported in the above table are corrected on a well-by-well basis for the variations in optical densities arising from the "cloudiness" of the inserted polystyrene disks and from the silicone grease used to affix the disks to the bottoms of the wells. Each well thus becomes its own control. The optical densities are also corrected for the fact that the disks tend to pick up a little color during the staining process with the amidoblack chromophore. The cell attachment experiment in this case was the standard assay for fibronectin activity using VERO cells. In order to further validate this particular assay, one bare lane was coated with ProNectin®F directly onto the polystyrene plate using standard solution coating methods. This acts as a check on the "temperament" of the particular batch of VERO cells used to conduct the assay.

The performance of ProNectin®F which was coated from solution onto polystyrene surfaces is unaffected by the presence or absence of processing aids added to the underlying polystyrene by the manufacturer. On the other hand, the performance of ProNectin®F which was dispersed into polystyrene powder and compression molded into films was seriously reduced by the presence of such processing aids. In the case of Amoco GR3-C7, the most likely cause of the degraded performance is believed to be the zinc stearate added as a mold release agent.

ProNectin®F. SLP3. and P-85 Surfactant

Polystyrene pellets without added zinc stearate, lubricants, or waxes (Amoco IR3-C0) were ground to a powder in a standard laboratory Waring blender using neat isopropanol as the slurrying agent. The recovered powder was further washed with isopropanol on a Buchner funnel, dried in air, and sieved to >100 mesh using American Standard stainless steel sieves. The additives used in these experiments were the protein polymers ProNectin®F and SLP3. The surfactant used was Pluronic P-85 from BASF Corporation. The protein polymers SLP3 and SLPF share a common backbone with the exception that SLPF includes a cell binding domain. Thus SLP3 serves as a negative control for the performance of the SLPF. The various additives were dissolved in 30 ml of formic acid (85%), slurried with 10 g of sieved polystyrene powder >100 mesh, and concentrated to dryness on a rotary evaporator. Several sample films from each lot of powder were compression molded, cell attachment assays were conducted on a single 96-well tissue

TABLE 3

Optical Densities of Cell Attachment Assays on Compression Molded Films with PnF.

| Sample | PnF [ppm] | Polymer Disks | N | OD [mean] | ± s | CV |
|---|---|---|---|---|---|---|
| Bare Plate | | | 8 | 0.000 | ±0.003 | n/a |
| Bare Plate | Solution coated 1 μg-PnF/ml | | 8 | 0.797 | ±0.037 | 5% |
| 102,028-1 | PS [IR3-C0] Solution coated 1 μg-PnF/ml | | 8 | 0.669 | ±0.070 | 10% |
| 102,028-9 | PS [GR3-C7] Solution coated 1 μg-PnF/ml | | 8 | 0.681 | ±0.074 | 11% |
| 102,028-1 | 000 | PS [Amoco IR3-C0] | 8 | 0.000 | ±0.010 | n/a |
| 102,028-9 | 000 | PS [Amoco GR3-C7] | 8 | 0.000 | ±0.028 | n/a |
| 102,028-2 | 200 | PS [Amoco IR3-C0] | 8 | 0.557 | ±0.046 | 8% |
| 102,028-10 | 200 | PS [Amoco GR3-C7] | 8 | 0.106 | ±0.117 | 111% |

culture plate, and a matrix of optical densities obtained according to the standard protocols described above.

TABLE 4

Cell Attachment Assays

| | PnF [ppm] | P-85 [ppm] | SLP3 [ppm] | N | OD [mean] | ± s | CV |
|---|---|---|---|---|---|---|---|
| 102,017-00 | Solution coated with 100 μl of 1 μg-PnF/ml | | | 8 | 0.608 | ±0.159 | 26% |
| 102,017-01 | -0- | -0- | 400 | 6 | 0.122 | ±0.034 | 28% |
| 102,017-02 | -0- | 400 | 400 | 6 | 0.116 | ±0.020 | 17% |
| 102,017-03 | 400 | -0- | -0- | 8 | 0.642 | ±0.079 | 12% |
| 102,017-04 | 50 | 100 | -0- | 8 | 0.166 | ±0.033 | 20% |
| 102,017-05 | 800 | 100 | -0- | 8 | 0.513 | ±0.144 | 28% |
| 102,017-06 | 200 | 200 | -0- | 8 | 0.116 | ±0.027 | 24% |
| 102,017-07 | -0- | 400 | -0- | 8 | 0.091 | ±0.020 | 22% |
| 102,017-08 | 100 | 400 | -0- | 8 | 0.100 | ±0.017 | 17% |

TABLE 4-continued

Cell Attachment Assays

| | PnF [ppm] | P-85 [ppm] | SLP3 [ppm] | N | OD [mean] | ± s | CV |
|---|---|---|---|---|---|---|---|
| 102,017-09 | 400 | 400 | -0- | 8 | 0.101 | ±0.017 | 17% |
| 102,017-10 | 200 | 800 | -0- | 8 | 0.095 | ±0.015 | 16% |
| 102,017-11 | 50 | 1600 | -0- | 6 | 0.115 | ±0.033 | 28% |
| 102,017-12 | 800 | 1600 | -0- | 6 | 0.178 | ±0.048 | 27% |

Optical densities were measured at 595 nm, which is to say that attached cells stain with a blue color. There exists a modest background optical absorbance in these measurements due to a slight opacity of the inserted disks as well as the presence of the silicone grease used as adhesive. The measured optical densities of the 102,017-02 and -03 samples serve as a measure of this background absorbance As can be seen in the data in the above table, the performance of the disks from sample 102,017-03 is indistinguishable from that of polystyrene disks which were coated with ProNectin®F from solution in aqueous lithium perchorate. Only low levels of the P-85 surfactant can be tolerated in combination with the ProNectin®F without seriously degrading the cell attachment performance of the ProNectin®F. Again, these results demonstrate the sensitivity of the cell attachment performance of the ProNectin®F to interferences from additives present in the polystyrene.

Deposition of ProNectin®F onto Polystyrene by Evaporative Coating

Experiment s were conducted using polystyrene pellets (Amoco IR3 -C0) from a lot without added zinc stearate, mineral oil, or wax. The native pellets were ground to a powder using neat isopropanol as the slurrying agent in a miniature Waring blender. The recovered powder was further washed with isopropanol on a Buchner funnel, air dried, and sieved to various mesh sizes. The ProNectin®F was dissolved in 30 ml of formic acid, slurried with 10 g of sieved polystyrene powder, and concentrated to dryness on a rotary evaporator. Several sample film from each lot of powder were compression molded, cell attachment assays were conducted on a single 96-well plate, and a matrix of optical densities was obtained using the standard protocol described above.

TABLE 5

Optical Densities of Cell Attachment Assays On Compression Molded PS With PnF

| | PnF [ppm] | PS Powder mesh range | N | OD [mean] | ± s | CV |
|---|---|---|---|---|---|---|
| Bare Plate | Optical blank, no cells | | 8 | 0.037 | ±0.002 | 4% |
| Bare Plate | Solution coated with 100 μl of 1 μg-PnF/ml | | 8 | 0.573 | ±0.024 | 4% |
| 103-64-00 | PS Optical & Stain blank; no cells | | 8 | 0.085 | ±0.035 | 41% |
| 103-64-00 | PS solution coated with 100 μl 1 μg-PnF/ml | | 8 | 0.600 | ±0.075 | 13% |
| 103-64-J | 150 | 20–40 | 8 | 0.500 | ±0.061 | 12% |
| 102-17-03 | 400 | >100 | 8 | 0.493 | ±0.069 | 14% |
| 103-64-A | 400 | >100 | 8 | 0.461 | ±0.045 | 10% |
| 103-64-B | 200 | >100 | 8 | 0.352 | ±0.086 | 24% |
| 103-64-C | 150 | >100 | 8 | 0.181 | ±0.055 | 30% |
| 103-64-F | 150 | 60–80 | 8 | 0.471 | ±0.097 | 20% |
| 103-64-G | 150 | 20–40 | 8 | 0.353 | ±0.074 | 21% |
| 103-64-D | 100 | >100 | 8 | 0.115 | ±0.056 | 49% |
| 103-64-E | 50 | >100 | 8 | 0.012 | ±0.049 | 408% |

Data from samples prepared with >100 mesh powder is especially well behaved with cell attachment performance decreasing monotonically with the concentration of applied ProNectin®F.

At 400 ppm PnF compression molded into this polystyrene powder, the performance of the disks is statistically indistinguishable from PnF at 1 μg/ml solution coated onto the same disks or onto the bare plate. Below 250–300 ppm, the performance begins to fall off.

The above data shows that PnF at 150 ppm on 60–80 mesh polystyrene powder performs as well as PnF at 400 ppm on >100 mesh. Thus the mesh size of the polystyrene powder appeared to be a determinant of the performance when ProNectin®F was deposited onto the polystyrene by evaporative coating.

Deposition of ProNectin®F onto Polyethylene by Evaporative Deposition

Experiments were conducted using low density polyethylene (PE) powder commercially available from Aldrich Chemical Company as catalog number 18,189-7. The powder is of unknown composition with respect to processing aids or stabilizers added by the manufacturer. In order to reduce the possibility of interferences by these additives, the PE powder was subjected to exhaustive extraction with boiling isopropanol for 24 hours in a Soxhlet apparatus. Recovered polyethylene powder was air dried before use. The ProNectin®F was dissolved in 30 ml of formic acid, slurried with 10 g of PE powder, and concentrated to dryness on a rotary evaporator. Several sample films from each lot of powder were compression molded, cell attachment assays were conducted on a single 96-well plate, and a matrix of optical densities was obtained using the standard protocol described above.

TABLE 6

| | Optical Densities of Cell Attachment Assays On Compression Molded PE With PnF. | | | | |
|---|---|---|---|---|---|
| | ProNectin ® F On Polyethelene Powder | N | OD [mean] | ± s | CV |
| Bare Plate | Optical blank | 8 | 0.032 | ±0.002 | 6% |
| Bare Plate | Solution coated with 100 μl of 1 μg-PnF/ml | 8 | 0.721 | ±0.022 | 3% |
| 103,064-00 | Solution coated with 100 μl of 1 μg-PnF/ml | 8 | 0.591 | ±0.052 | 9% |
| 103,064-01 | 600 ppm | 8 | 0.092 | ±0.060 | 65% |
| 103,064-02 | 400 ppm | 8 | 0.085 | ±0.061 | 72% |
| 103,064-03 | 200 ppm | 8 | 0.169 | ±0.100 | 59% |
| 103,064-04 | 150 ppm | 8 | 0.138 | ±0.084 | 75% |
| 103,064-05 | 100 ppm | 8 | 0.084 | ±0.063 | 75% |
| 103,064-06 | 50 ppm | 8 | 0.066 | ±0.067 | 102% |
| 103,064-00 | 00 ppm | 8 | 0.000 | ±0.036 | n/a |

Clearly, ProNectin®F which was evaporatively coated onto polyethylene powder and compression molded into films is active in a cell attachment assay using VERO cells. The degree of attachment activity is lower compared to that observed on polystyrene. The differences in performance between polystyrene and polyethylene are believed to result from additives in the polyethylene which were not removed in the washing step.

Deposition of ProNectin®F onto Polypropylene and Polymethylmethacrylate by Vortex Dilution.

Polypropylene non-woven fabric was recovered from the liner of a disposable diaper and washed exhaustively with isopropanol in Soxhlet apparatus for 24 hours. This fabric represents a conveniently available source polypropylene with a high surface area suitable for coating with ProNectin®F. Coating was conducted using the modified vortex dilution technique as described in the section entitled “Effects of Additives in the Polystyrene”. Polymethylmethacrylate (Aldrich Chemical Company catalog number 18,224-9) as a medium molecular weight powder was used without additional purification. Coating was conducted using the modified vortex dilution technique.

Several sample films from each lot of powder were compression molded, cell attachment assays were conducted on a single 96-well plate, and a matrix of optical densities was obtained using the standard protocol described above.

TABLE 7

| Deposition of ProNectin ® F onto Polypropylene and Polymethylmethacrylate. | | | | | | |
|---|---|---|---|---|---|---|
| Sample | PnF [ppm] | Polymer Disks | N | OD [mean] | ± s | CV |
| Bare Plate | | | 8 | 0.000 | ±0.003 | n/a |
| Bare Plate | Solution coated 1 μg-PnF/ml | | 8 | 0.797 | ±0.797 | 5% |
| 102,028-1 | 000 | PS [Amoco IR3-C0] | 8 | 0.000 | ±0.010 | n/l |
| 102,028-2 | 200 | PS [Amoco IR3-C0] | 8 | 0.557 | ±0.046 | 8% |
| 102,028-7 | 000 | Poly[Methyl Methacrylate] | 8 | 0.000 | ±0.038 | n/l |
| 102,028-8 | 200 | Poly[Methyl Methacrylate] | 8 | 0.435 | ±0.050 | 11% |
| 102,028-11 | 000 | Polypropylene | 8 | 0.000 | ±0.042 | n/a |
| 102,028-12 | 230 | Polypropylene | 8 | 0.252 | ±0.128 | 51% |

These results showed that ProNectin®F can be compression molded into polypropylene and polymethylmethacrylate films. Neither the polypropylene nor the polymethylmethacrylate was of known composition with respect to low level concentrations of additives and surfactants. These particular samples of polymers were used because they were readily available and not because they were known to be optimal for this application. In any case, these samples of polymers showed cell attachment activity when compression molded with ProNectin®F.

Effect of Deposition Methods and Mesh Size

Experiments were conducted using polystyrene pellets (Amoco IR3-C0) from a lot without added zinc stearate, mineral oil, or wax. The native pellets were reduced to a powder by dry grinding in a coffee grinder. The recovered powder was washed with isopropanol on a Buchner funnel, air dried, and sieved to various mesh sizes. The ProNectin®F was deposited onto the polystyrene powders using one of three methods: evaporation of the formic acid in the absence of water, referred to as “Dry” rotovap; evaporation of the formic acid after the addition of 5 ml of water, referred to as “Wet” rotovap; and dilution of the formic acid with water under vortexing conditions, referred to as “Vortex” dilution. Several sample films from each lot of powder were compression molded, cell attachment assays were conducted on a single 96-well plate, and a matrix of optical densities was obtained using the standard protocol described above.

TABLE 8

Optical Densities of Cell Attachment Assays On Compression Molded PS With PnF.

| Sample | PnF [ppm] | Deposition Method | PS Powder mesh range | N | OD [mean] | ± s | CV |
|---|---|---|---|---|---|---|---|
| 103,065-00 | Optical blank, cells & stain | | | 8 | 0.000 | ±0.032 | n/a |
| 103,065-00 | Solution coated with 100 μl of 1 μg-PnF/ml | | | 8 | 0.655 | ±0.099 | 15% |
| 103,065-A | 150 | Dry Rotovap | >100 | 8 | 0.112 | ±0.049 | 44% |
| 103,065-B | 150 | Wet Rotovap | >100 | 8 | −0.008 | ±0.051 | n/a |
| 103,065-C | 150 | Vortex Dil'n | >100 | 8 | 0.468 | ±0.112 | 24% |
| 103,065-D | 150 | Dry Rotovap | 60–80 | 8 | 0.151 | ±0.045 | 30% |
| 103,065-E | 150 | Wet Rotovap | 60–80 | 8 | 0.335 | ±0.083 | 25% |
| 103,065-F | 150 | Vortex Dil'n | 60–80 | 8 | 0.532 | ±0.071 | 13% |
| 103,065-G | 150 | Dry Rotovap | 20–40 | 8 | 0.239 | ±0.044 | 18% |
| 103,065-H | 150 | Wet Rotovap | 20–40 | 8 | 0.102 | ±0.081 | 79% |
| 103,065-I | 150 | Vortex Dil'n | 20–40 | 8 | 0.410 | ±0.043 | 10% |
| 103,065-J | 150 | Wet Rotovap | 40–60 | 8 | 0.149 | ±0.72 | 408% |

The data in Table 8 showed that the most efficient utilization of ProNectin®F coated onto polystyrene powders comes about using the vortex dilution method. The mesh size of the polystyrene powder did not seem to be a major determinant of the outcome of the vortex dilution coating process. The use of mixed mesh polystyrene powders eased the preparation of these powders because the useable fraction ground powder increases with the broader mesh range.

Water present during evaporative deposition has an effect on the outcome of the coating process. This observation could explain variablility observed in some of the evaporative coating experiments. Variable amounts of water could enter the rotary evaporator from room ambient water vapor through accidental leaks or through sparging of the rotary evaporator apparatus with air during the evaporation process.

Deposition of ProNectin®F onto Polystyrene by Vortex Dilution Coating

Experiments were conducted using polystyrene (PS) pellets (Amoco IR3-C0) from a lot without added zinc stearate, mineral oil, or wax. The native pellets were ground to a powder in a miniature Waring blender without suspending solvent. The recovered powder was washed with isopropanol on a Buchner funnel, air dried, and sieved to >20 mesh. The ProNectin®F was dissolved in 15 ml of formic acid, slurried with 5 g of sieved polystyrene powder, agitated on a vortex mixer, and diluted with 45 ml of deionized water. The recovered polystyrene powder was collected on a Buchner funnel and dried in air. Several sample films from each lot of powder were compression molded, cell attachment assays were conducted on a single 96-well plate, and a matrix of optical densities was obtained using the standard protocol described above.

TABLE 9

Optical Densities of Cell Attachment Assays On Compression Molded PS With PnF

| | PnF [ppm] | PS Powder mesh range | N | OD [mean] | ± s | CV |
|---|---|---|---|---|---|---|
| Bare Plate | Optical blank, no cells or stain | | 8 | 0.037 | ±0.001 | 3% |
| Bare Plate | Solution coated with 100 μl of 1 μg-PnF/ml | | 8 | 0.799 | ±0.026 | 3% |
| 103-66-00 | PS Optical blank, no cells or stain | | 8 | 0.007 | ±0.016 | 229% |
| 103-66-00 | PS blank, cells and stain | | 8 | 0.022 | ±0.012 | 55% |
| 103-66-00 | Solution coated with 100 μl of 1 μg-PnF/ml | | 8 | 0.747 | ±0.052 | 7% |
| 103-66-A | 300 | >20 | 8 | 0.516 | ±0.048 | 9% |
| 103-66-B | 250 | >20 | 8 | 0.641 | ±0.073 | 11% |
| 103-66-C | 200 | >20 | 8 | 0.627 | ±0.068 | 11% |
| 103-66-D | 150 | >20 | 8 | 0.650 | ±0.057 | 9% |
| 103-66-E | 100 | >20 | 8 | 0.544 | ±0.067 | 12% |
| 103-66-F | 50 | >20 | 8 | 0.592 | ±0.060 | 10% |

ProNectin®F retained its activity down to 50 ppm. The combination of mixed mesh powders with vortex dilution deposition is extremely efficacious in depositing PnF in active form.

The reason for the reduced effectiveness of evaporative deposition compared to vortex deposition may be hydrolysis of the protein. The efficacy of vortex deposition bodes very well for the economics of the process.

Compression Molding of Polystyrene Containing ProNectin L

Experiments were conducted using polystyrene pellets from a lot without added zinc stearate, mineral oil, or wax. The native pellets were reduced to a powder by dry grinding in a coffee grinder. The recovered powder was washed with isopropanol on a Buchner funnel, air dried, and sieved to various mesh sizes. The ProNectin®L (PnL or SLPL 3.0) was deposited onto the polystyrene powder of 60–80 mesh using the vortex dilution technique. Several sample films from each of lot of powder were compression molded using the standard protocol descibed above.

TABLE 10

Optical Densities of Cell Attachment Assays On Compression Molded PS With ProNectin ® L.

| | PnL [ppm] | Deposition Method | PS Powder mesh range | N | OD [mean] | ± s | CV |
|---|---|---|---|---|---|---|---|
| Bare plate | Optical blank, cells & stain | | | 8 | 0.000 | ±0.014 | n/a |
| Bare plate | Solution coated with 100 μl of 1 μg-PnF/ml | | | 8 | 0.767 | ±0.106 | 14% |
| 103,067-00 | PS optical blank, cells & stain | | | 6 | 0.000 | ±0.016 | n/a |
| 103,067-00 | PS, solution coated with 100 μl of 1 μg-PnF/ml | | | 8 | 0.797 | ±0.144 | 18% |
| 103,065-A | 500 | Vortex | 60–80 | 8 | 0.052 | ±0.038 | 73% |
| 103,065-B | 550 | Vortex | 60–80 | 8 | 0.043 | ±0.043 | 100% |
| 103,065-C | 150 | Vortex | 60–80 | 8 | 0.046 | ±0.031 | 67% |
| 103,065-C1 | 150 | Vortex | 60–80 | 6 | 0.342 | ±0.106 | 31% |

The cell attachment experiment in this case was the standard assay for laminin activity using RD-P56 cells, described below. In order to further validate this particular assay, one bare lane was coated with ProNectin®L directly onto the polystyrene plate using standard solution coating methods. This acts as a check on the "temperment" of the particular batch of RD-P56 cells used to conduct the assay.

This data shows that ProNectin®L can survive the conditions of the compression molding process. After drying in air, the vortex dilution coated polystyrene powders retained a slight odor of formic acid. The sample 103,067-C1 was compression molded as it stood. The other samples were sparged with a stream of dry nitrogen until all odor of formic acid was removed. It could be that the IKVAV (SEQ ID NO:20) sequences of the ProNectin®L in sample 103,067-C1 were stabilized towards thermal degradation by neutralization of the lysines with this residual formic acid. In particular, more reproducible results were obtained when non-volatile acids such as toluene sulfonic acid were added to the compression molding mixtures.

Attachment Assay Using RD-P56 Cells

The silicone grease "adhesive" used to affix compression molded test disks to the tissue culture plates was prepared by diluting Dow Cornin High Vacuum Grease with cyclohexane to a final concentration of 25% w/v, centrifuging to compact the silica filler, and retaining the supernatant. To each well of a 96-well tissue culture plate which is to receive a test disk was added 25 μl of the silicone adhesive solution. The plate was then dried overnight in a vacuum oven at 40° C. One lane of the plate, as a positive control, was solution coated with ProNectin®L using the standard protocols described above. Best results were obtained when all wash and aspiration steps were performed using a Biotek 403H automated plate washer with settings: dispense height=10; plate height=100; dispense volume=200 μl; and number of washes=2.

While the positive control lane was being solution coating with ProNectin®L, the 7 mm diameter test disks were placed into 5 dram vials and washed 3 times with 5 ml of 1× calcium-magnesium free phosphate buffered saline (cmf PBS). The test disks were then placed into each well and gently pressed into the siicone grease which had been layered on the bottom of the well. After mounting the test disks into the plate, they were washed twice with 100 μl of 1× cmf PBS. At this time, the background absorbances were read using a Titertek Plate Reader at 595 nm. Blocking solution (2mg of bovine serum albumin per milliliter of cmf PBS), 100 μl, was added to each well and incubated for 30 minutes at 370° C. The blocking solution was aspirated and the plate rinsed once with cmf PBS. RD-P56 cells, $1\times10^5$ cells, were added to each well using culture media without fetal bovine serum and the plate incubated for 1 hour at 37° C. The media containing the cells was aspirated and the plate rinsed twice with cmf PBS. Fixative solution (3.7% formaldehyde in 1× cmf PBS) was added to each well and incubated for 20 minutes at room ambient temperature. The fixative solution was aspirated and the plate was rinsed once with cmf PBS. Staining solution (0.1% amido black in 40% methanol- 10% acetic acid) was added, and the plate was incubated for 15 minutes at room ambient temperature. The plate was then rinsed with deionized water to remove all soluble dye. The plate was dried over night at room ambient temperature. Elution buffer (10% aqueous sodium dodecyl sulfate) was added and the absorbance read using the Titertek Plate Reader at 595 nm.

Reproducibility of Coatings Deposited by Vortex Dilution

Experiments were conducted using polystyrene pellets (Amoco IR3-C0) from a lot without added zinc stearate, mineral oil, or wax. The native pellets were ground to a powder in a miniature Waring blender without suspending solvent. The recovered powder was washed with isopropanol on a Buchner funnel, air dried, and sieved to >20 mesh. The ProNectin®F was dissolved in 15 ml of formic acid, slurried with 5 g of sieved polystyrene powder, agitated on a vortex mixer, and diluted with 45 ml of deionized water. The recovered polystyrene powder was collected on a Buchner funnel and dried in air. Three independent preparations of polystyrene powder coated with ProNectin®F were conducted and sampled individually for compression molding. The three preparations were combined, physically mixed, and again sampled for compression molding.

Several sample films from each lot of powder were compression molded, cell attachment assays were conducted on a single 96-well plate, and a matrix of optical densities was obtained using the standard protocol described above.

TABLE 11

Optical Densities of Cell Attachment Assays on Compression Molded PS with PnF.

| | PnF [ppm] | PS Powder mesh range | N | OD [mean] | ± s | CV |
|---|---|---|---|---|---|---|
| Bare Plate | Solution coated with 100 μl of 1 μg-PnF/ml | | 8 | 0.547 | ±0.019 | 3% |
| 103-069-00 | PS Optical blank, no cells or stain | | 7 | 0.000 | ±0.024 | n/a |
| 103-069-00 | PS blank, cells and stain | | 8 | 0.555 | ±0.036 | 6% |
| 103-069-A | 200 | >20 | 8 | 0.473 | ±0.031 | 9% |
| 103-069-B | 200 | >20 | 8 | 0.526 | ±0.046 | 7% |
| 103-069-C | 200 | >20 | 8 | 0.521 | ±0.071 | 14% |
| 103-069-D | 200 | >20 | 7 | 0.535 | ±0.033 | 6% |

The data in Table 11 showed that multiple preparations of a coated polystyrene powder gave the same result. The coating process appeared reproducible. The mean optical density for preparations A, B, C & D, which is [A+B+C], was 0.520±0.047. The results in Table 11 showed that the application of ProNectin®F to polystyrene powder can be accomplished with high reproducibility on a batch-to-batch basis. Establishing such reproducibility is important to the design of coating processes at a commercial scale.

Usable Dispersing Agents

Experiments were conducted using polystyrene pellets (Amoco IR3-C0) from a lot without added zinc stearate, mineral oil, or wax. The native pellets were ground to a powder in a miniature Waring blender without suspending solvent. The recovered powder was washed with isopropanol on a Buchner funnel, air dried, and sieved to >20 mesh. The ProNectin®F was dissolved in 15 ml of formic acid, slurried with 5 g of sieved polystyrene powder, agitated on a vortex mixer, and diluted with 45 ml of deionized water. The recovered polystyrene powder was collected on a Buchner funnel and dried in air.

Polystyrene powder which was precoated with ProNectin®F was then challenged with a wash with isopropanol alone and in combination with reagents which are potentially useful as agents for the dispersal of ProNectin®F into polystyrene melts. The reagents, each at 200 ppm in isopropanol (103,069-E), were phenyltriethoxysilane (103, 069-F), tetraisopropoxytitanium (IV) (103,069-G), isopropoxytris isosteroyl titanate (Kenrich KR-TTS) (103,069-I), neopentyl (diallyl) oxy-[trix(dioctyl)pyrophosphato] titanate (Kenrich LICA-38) (103,069-H).

Preparation of compression molded film samples and a cell attachment assay were conducted using standard protocols described above.

TABLE 12

Optical Densities of Cell Attachment Assays on Compression Molded PS with PnF.

| | PnF [ppm] | PS Powder mesh range | N | OD [mean] | ± s | CV |
|---|---|---|---|---|---|---|
| Bare Plate | Solution coated with 100 μl of 1 μg-PnF/ml | | 8 | 0.547 | ±0.019 | 3% |
| 103,069-00 | PS Optical blank, no cells or stain | | 7 | 0.000 | ±0.024 | n/a |
| 103,069-00 | PS blank, cells and stain | | 8 | 0.555 | ±0.036 | 6% |
| 103,069-A | 200 | | 8 | 0.473 | ±0.031 | 9% |
| 163,069-E | 200 | | 8 | 0.482 | ±0.073 | 15% |
| 103,069-F | 200 | | 7 | 0.512 | ±0.040 | 8% |
| 103,069-G | 200 | | 8 | 0.509 | ±0.048 | 10% |
| 103,069-H | 200 | | 7 | 0.490 | ±0.067 | 14% |
| 103-069-I | 200 | | 8 | 0.510 | ±0.042 | 8% |

The data in table 12 showed that these dispersing agents do not interfere with the cell attachment function of the ProNectin®F when they are added to the coated polystyrene powder at these concentrations. These four dispersing agents thus may be considered as aids for achieving improved mixing of the ProNectin®F throughout the polystyrene melt during a thermolding process.

Thermal Stress Matrix for Unstabilized ProNectin®F

Experiments were conducted using Polystyrene pellets from a lot without added zinc stearate, mineral oil, or wax. The native pellets were ground to a powder in a miniature Waring blender without suspending solvent. The recovered powder was washed with isopropanol on a Buchner funnel, air dried, and sieved to >20 mesh. The ProNectin®F (1.0 mg) was dissolved in 15 ml of formic acid, slurried with 5 g of sieved polystyrene powder, agitated on a vortex mixer, and diluted with 45 ml of deionized water. The recovered polystyrene powder was collected on a Buchner funnel and dried in air without agitation. This powder was designated as having been coated at 200 ppm.

A sample (2.0 g) of polystyrene powder coated with ProNectin®F (200 ppm) was placed into a Pyrex glass tube (16 mm ×100 mm); sealed with a rubber septum cap, sparged with nitrogen, and heated in a thermostatted oil bath preheated to the required temperature for varying lengths of time. Several sample films from each lot of powder were compression molded, cell attachment assays were conducted on a single 96-well plate, and a matrix of optical densities was obtained using the standard protocol described above.

TABLE 13

Optical Densities of Cell Attachment Assays.

| | PnF [ppm] | Time [min] | Temp. [°C.] | N | OD [mean] | ± s | CV |
|---|---|---|---|---|---|---|---|
| Bare Plate | Solution coated with 100 μl of 1 μg-PnF/ml | | | 8 | 0.628 | ±0.008 | 1% |
| 103-075-1 | 200 | 1/4 | 150° | 8 | 0.530 | ±0.099 | 19% |
| 103-075-2 | 200 | 5 | 150° | 8 | 0.488 | ±0.069 | 14% |
| 103-075-3 | 200 | 80 | 150° | 8 | 0.200 | ±0.106 | 53% |
| 103-075-4 | 200 | 20 | 175° | 8 | 0.083 | ±0.042 | 51% |
| 103-075-5 | 200 | 10 | 200° | 8 | 0.066 | ±0.036 | 55% |
| 103-075-6 | 200 | 20 | 200° | 8 | 0.036 | ±0.031 | 86% |
| 103-075-7 | 200 | 40 | 200° | 8 | 0.010 | ±0.020 | 200% |
| 103-075-8 | 200 | 20 | 225° | 8 | 0.008 | ±0.011 | 138% |
| 103-075-9 | 200 | 5 | 250° | 8 | 0.011 | ±0.014 | 127% |
| 103,075-10 | 200 | 40 | 250° | 8 | 0.0003 | ±0.011 | n/a |
| 103,075-11 | 200 | 10 | 275° | 8 | 0.0003 | ±0.015 | n/a |

The performance of the compression molded disks of polystyrene in the cell attachment assay decreased with increasing time and with increasing temperature in a complex manner. The amount of ProNectin®F required in the initial formulation will be dictated by the required performance of the final article and by the time-temperature history of the injection molding process.

The time-temperature experiments represent a response surface which can be fitted by multivariate regression analysis. A model was defined which assumes a first order reaction for thermal degradation with the rate constant being exponential in temperature. The fit of this model is R2=0.963, and the equation has the satisfying property of fitting only three adjustable parameters to the 11 data points. The following parameters can be added together to form an equation which can be used to interpolate points on the time-temperature response surface.

Parameter estimates for Ln[Ln(A0/A)] R2 = 0.963

| Term | Coefficient | Std Error | t Ratio | Prob > \|t\| |
|---|---|---|---|---|
| Intercept | 12.256021 | 1.49242 | 8.21 | 0.0000 |
| Ln[t] | 0.7049276 | 0.08461 | 8.33 | 0.0000 |
| 1/°K. | −6429.016 | 672.61 | −9.56 | 0.0000 |

Relationship of Solution Concentrations to Surface Deposition

Films were compression molded from polystyrene pellets (Amoco IR3-C0) and cut into strips 1 cm ×2cm. In order to reduce the fluorescent background due to low level contaminants as much as possible, the films were extracted in concentrated hydrochloric acid for 18 hours at 80° C. The disks were rinsed in deionized water and solution coated with ProNectin®F using a solution of PnF (1 mg/mil) in 88% formic acid serially diluted out to the final concentrations with 1× phosphate buffered saline. Polystyrene films were left in contact with the diluted coating solutions for 2 hours on a nutator to provide agitation. The films were recovered, rinsed in deionized water, and air dried. Proteins on the surface of the each piece of film were hydrolysed by exposure to the vapors of constant boiling hydrochloric acid in an evacuated container for 18 hours at 80° C. The vials were opened and placed in a vacuum oven at 40° C. for 2 hours to remove water and hydrogen chloride. The residue of hydrolysed amino acids was dissolved using 1 ml of 100 mM pH9 borate buffer. Fluorescence was developed by adding 1 ml of a solution of fluorescamine (0.1 mg/ml) in acetone. Fluorescence was read using a Turner filter fluorimeter (excitation 390 nm; emission 475 nm). Fluorescent standards were prepared using synthetic mixtures of glycine, alanine, and serine in a molar ratio corresponding to the PnF. In all cases the amount of PnF (Concsolution X Vol.) available in the diluted solutions to each piece of polystyrene film was much greater than the amount of PnF (Concsurface X Area) which ended up actually absorbed to the surface. This ratio is indicated at each data point of the graph. The means and standard deviations for each data point were obtained by conducting multiple assays on 6 to 8 independent samples.

Films were compression molded from polystyrene pellets (Amoco IR3-C0). Disks (7 mm dia.) were punched out using a "one-hole" paper punch. These disks were cleaned and coated with ProNectin®F as described above. The disks were mounted in a 96-well tissue culture plate using our standard methods. One lane of blank well in the same plate were solution coated with PnF. The cell attachment assay was conducted according to the standard protocol described above.

TABLE 14

Surface Concentration vs. Solution Concentration.

| PnF Solution | Excess PnF | PnF Surface ($\mu$g/cm$^2$-Ps) | | Cell Attachment Abs @ 595 | |
|---|---|---|---|---|---|
| ($\mu$g/ml) | Available | Mean | ± Std Dev | Mean | ± Std Dev |
| 100.00 | 802x | 0.624 | ±0.157 | 0.59 | ±0.06 |
| 10.00 | 140x | 0.479 | ±0.145 | 0.55 | ±0.04 |
| 1.00 | 48x | 0.104 | ±0.087 | n/d | n/d |
| 0.20 | 2.0x | 0.084 | ±0.085 | 0.52 | ±0.02 |
| 0.10 | 8.2x | 0.061 | ±0.066 | 0.29 | ±0.05 |
| 0.02 | 3.2x | 0.031 | ±0.062 | 0.00 | n/d |
| 0.00 | n/a | 0.000 | ±0.077 | | |

The deposition of PnF onto polystyrene surfaces showed a sigmoidal profile of surface concentrations versus solution concentrations which is a characteristic of Langmuirian absorption processes.

At high solution concentrations, the amount deposited onto the surface of the polystyrene reaches a plateau. The measured surface concentrations in this plateau region were very close to our estimate of monolayer coverage based on a consideration of the geometry of the ProNectin®F molecule.

Cell attachment activity of the coated polystyrene was remarkably insensitive to coverage of the polystyrene by PnF. Cell attachment reaches a plateau at about monolayer coverage of the surface by PnF. Half of the cell attachment activity persists down to 0.1 monolayer on the specially cleaned polystyrene surfaces. Cell attachment activity did not persist to such low degrees of coverage when PnF was deposited onto a standard commerical grade polystyrene such as Amoco 1R3-C0. The data in Table 14 relating solution concentrations of ProNectin®F to surface deposition and cell attachment performance is essential to designing a commerical coating process.

Stabilization of ProNectin®F

Experiments were conducted using polystyrene pellets from a lot without added zinc stearate, mineral oil, or wax. The native pellets were ground to a powder in a miniature Waring blender without suspending solvent. The recovered powder was washed with isopropanol on a Buchner funnel, air dried, and sieved to >20 mesh. The ProNectin®F (1.0 mg) was dissolved in 15 ml of formic acid, slurried with 5 g of sieved polystyrene powder, agitated on a vortex mixer, and diluted with 45 ml of deionized water. In another experiment, the ProNectin®F (1.0 mg) and calcium oxide (1.0 mg) was dissolved in the formic acid. In both cases, the recovered polystyrene powder was collected on a Buchner funnel and dried in air without agitation. In one case, the polystyrene powder was compression molded before all residues of formic acid were evaporated. These powders were designated as being coated at 200 ppm ProNectin®F.

Several sample films from each lot of powder were compression molded, cell attachment assays were conducted on a single 96-well plate, and a matrix of optical densities was obtained using the standard protocol described above.

TABLE 15

Optical Densities of Cell Attachment Assays Using PnF (200 ppm) On PS

| | Comments | Time [min] | Temp. [°C.] | N | OD [mean] | ± s | CV |
|---|---|---|---|---|---|---|---|
| Bare Plate | Solution coated with 100 $\mu$l of 1 $\mu$g-PnF/ml | | | 5 | 0.761 | ±0.005 | 1% |
| 103,066-C | Std Vortex | 1/4 | 150° | 3 | 0.681 | ±0.059 | 9% |
| 103,079-2 | Std Vortex | 5 | 150° | 4 | 0.516 | ±0.055 | 11% |
| 103,079-3 | Formic Residues | 1/4 | 150° | 3 | 0.204 | ±0.088 | 43% |
| 103,079-4 | Ca+2 | 1/4 | 150° | 3 | 0.729 | ±0.040 | 5% |

Occasionally, difficulties were encountered in the cell attachment assays; especially with reduced optical densities for the positive controls. Some of these difficulties might have been a result of contamination by cyclohexane. Cyclohexane is used to apply the silicone grease which serves as an adhesive to afix the polystyrene disks to the bottoms of the wells on the 96-well plate. Removal of the cyclohexane is best achieved using a vacuum oven.

The presence of formic acid residues on samples of polystyrene coated with ProNectin®F leads to reduced O.D.s upon compression molding compared to fully dried samples. This result is in direct contrast to the result described above in the case of ProNectin®L.

The presence of calcium formate in the coating recipe appears to have a protective effect on the ProNectin®F during the compression molding operation.

Lot Reproducibility & Rinses with Calcium Salts

Experiments were conducted using polystyrene pellets from a lot without added zinc stearate, mineral oil, or wax. The native pellets were ground to a powder in a miniature Waring blender without suspending solvent. The recovered powder was washed with isopropanol on a Buchner funnel, air dried, and sieved to >20 mesh. Samples of ProNectin®F from three separates lots were evaluated for their cell attachment efficacy. The ProNectin®F (1.0 mg) was dissolved in 15 ml of formic acid, slurried with 5 g of sieved polystyrene powder, agitated on a vortex mixer, and diluted with 45 ml of deionized water. The polystyrene powder was recovered by filtration, sucked as dry as possible on the filter, and dried in air. In another experiment, the polystyrene powder was recovered by filtration, rinsed with water, sucked as dry as possible, and dried in air.

In another group of experiments, samples of a single lot of ProNectin®F (1.0 mg) were dissolved in three solvents: 85% formic acid, 6M aqueous urea, and 4.5M aqueous lithium perchlorate. Coating of the polystyrene powder was conducted as described above. Samples were recovered by filtration, rinsed with 100 mM aqueous calcium chloride solutions, sucked as dry as possible on the filter, and dried in air.

Several sample films from each lot of powder were compression molded, cell attachment assays were conducted on a single 96-well plate, and a matrix of optical densities was obtained using the standard protocol described above.

TABLE 16

Optical Densities of Cell Attachment Assay

| | Comments | Time [min] | Temp. [°C.] | N | OD [mean] | ± s | CV |
|---|---|---|---|---|---|---|---|
| Bare Plate | Solution coated with 100 $\mu$l of 1 $\mu$g-PnF/ml | | | 8 | 0.491 | ±0.041 | 1% |
| 103,080-C | Lot #26; Formic | 1/4 | 150° | 8 | 0.356 | ±0.079 | 27% |
| 103,080-D | Lot #27; Formic | 1/4 | 150° | 7 | 0.384 | ±0.079 | 11% |
| 103,066-C | Lot #24; Formic | 1/4 | 150° | 8 | 0.374 | ±0.065 | 112% |
| 013,080-H | Lot #26; Formic; Water Rinse | 1/4 | 150° | 7 | 0.361 | ±0.132 | 32% |
| 103,080-I | Lot #26; Formic; $CaCl_2$ Rinse | 1/4 | 150° | 8 | 0.494 | ±0.043 | 13% |
| 103,080-J | Lot #26; Urea; $CaCl_2$ Rinse | 1/4 | 150° | 8 | 0.548 | ±0.036 | 22% |
| 103,080-K | Lot #26; $LiClO_4$; $CaCl_2$ Rinse | 1/4 | 150° | 8 | 0.519 | ±0.059 | 15% |

Samples of ProNectin®F from three separate fermentation lots are all functionally equivalent in the cell attachment assay after being coated onto polystyrene powders and compression molded into films.

These data show that solutions of ProNectin®F made up in 85% formic acid, 6M aqueous urea, and 4.5M aqueous lithium perchlorate were all functionally equivalent when used in the vortex dilution method of coating polystyrene powders.

The ability to substitute 6M aqueous urea is of great significance to the design and cost of a large scale coating process for polystyrene powders. Avoiding corrosive reagents in the process means that the large scale process equipement can be made of less expensive materials of construction.

Calcium Stabilization of ProNectin®F

Experiments were conducted using polystyrene (PS) pellets from a lot without added zinc stearate, mineral oil, or wax. The native pellets were ground to a powder in a miniature Waring blender without suspending solvent. The recovered powder was washed with isopropanol on a Buchner funnel, air dried, and sieved to >20 mesh. ProNectin®F (8.0 mg) was dissolved in 8 ml of formic acid and added to 400 ml of 150 mM NaCl solution contained in a 1000 ml Erlenmeyer flask fitted with a magnetic stirrer to yield a final concentration of 20 $\mu$g-PnF/ml. The polystyrene powders were prewetted with mixtures of methanol by immersing the PS in the methanol and applying house vacuum to the head space. Excess methanol was decanted from the wetted PS powders before the PS powders were added to the diluted solution of PnF. The slurry was stirred for 2 hours at room temperature before being filtered. One sample of powder was rinsed with water, the sample of PS powder was resuspended in 100 mM calcium chloride solution, which was adjusted to pH 7, stirred for 10 minutes, and filtered. Theses samples of PS powder were then resuspended in 10 mMolar calcium chloride solution, which was adjusted to pH 7, stirred for 10 minutes, filtered, sucked as dry as possible and dried in air. A sample (2.0 g) of polystyrene powder coated with ProNectin®F was placed into a Pyrex glass tube (16 mm ×00mm); sealed with a rubber septum cap, sparged with nitrogen, and heated in a thermostatted oil bath preheated to 200° C. for 5 minutes. Several sample films from each lot of powder were compression molded, cell attachment assays were conducted on a single 96-well plate, and a matrix of optical densities was obtained using the standard protocol described above. $Ca^{+2}$

TABLE 17

Optical Densities of Cell Attachment Assays

| | Comments | Time [min] | Temp. [°C.] | N | OD [mean] | ± s | CV |
|---|---|---|---|---|---|---|---|
| Bare Plate | Solution coated with 100 μl of 1 μg-PnF/ml | | | 8 | 0.549 | ±0.044 | 1% |
| 103,081-1A | Wetted 100% MeOH | 1/4 | 150° | 8 | 0.531 | ±0.094 | 18% |
| 103,081-1B | Wetted 100% MeOH | 5 | 200° | 8 | 0.135 | ±0.066 | 49% |
| 103,081-2B | Wetted 100% MeOH; Ca+2 | 5 | 200° | 7 | 0.194 | ±0.052 | 27% |
| 103,081-3A | Wetted 50% MeOH | 1/4 | 150° | 8 | 0.560 | ±0.062 | 11% |
| 103,081-3B | Wetted 50% MeOH | 5 | 200° | 8 | 0.065 | ±0.073 | 112% |
| 103,081-4A | Wetted 50% MeOH; Ca+2 | 1/4 | 150° | 8 | 0.554 | ±0.079 | 14% |
| 103,081-4B | Wetted 50% MeOH; Ca+2 | 5 | 200° | 7 | 0.311 | ±0.099 | 32% |
| 103,081-5A | Dry Powder | 1/4 | 150° | 8 | 0.519 | ±0.065 | 13% |
| 103,081-5B | Dry Powder | 5 | 200° | 8 | 0.172 | ±0.037 | 22% |
| 103,081-6A | Dry Powder; Ca+2 | 1/4 | 150° | 8 | 0.581 | ±0.050 | 9% |
| 103,081-6B | Dry Powder; Ca+2 | 5 | 200° | 8 | 0.418 | ±0.064 | 15% |

ProNectin®F may be stabilized towards thermally induced deactivation. Rinsing the coated PS powders with calcium chloride solution produce samples which retained much more activity than the standard samples after a thermal challenge of 5 minutes at 200° C.

The coating methodology used in preparing these samples is important because it can be scaled for working with larger lots of polystyrene powder. The engineering aspects of working with stirred slurries of powders is well understood and is scaleable to larger sizes in a straightforward manner. The "tool", the coating technique, now exists which makes it possible to work with multi-kilogram lots of polystyrene powders.

Prewetting the polystyrene with methanol was conducted in order to improve the contact between the aqueous solution of PnF and the hydrophobic surface of the polystyrene powders. Such a prewetting is clearly counterindicated by the data in this table. Coating of dry polystyrene powders performed better. The effect was more apparent in those samples which were "stressed" at high temperatures.

Thermal Stress Matrix for Calcium Stabilized ProNectin®F

Experiments were conducted using Polystyrene pellets from a lot without added zinc stearate, mineral oil, or wax. The native pellets were ground to a powder in a miniature Waring blender without suspending solvent. The recovered powder was washed with isopropanol on a Buchner funnel, air dried, and sieved to >20 mesh.

ProNectin®F (8.0 mg) was dissolved in 8 ml of 10 molar aqueous urea and diluted into 400 ml of 150 mmolar aqueous sodium chloride solution contained in a 1000 ml Erlenmeyer flask. Polystyrene powder (20 g) was added as a dry powder, and was stirred for 1 hour at room temperature. The recovered polystyrene powder was collected on a Buchner funnel, washed with 100 mM calcium chloride solution, washed with 10 mM calcium chloride solution, sucked as dry as possible, and dried in air without agitation. The loading of ProNectin®F onto this polystyrene powder was estimated from previous measurements of the surface area of the powder and the adsorption isotherm.

A sample (2.0 g) of polystyrene powder coated with ProNectin®F (200 ppm) was placed into a Pyrex glass tube (16 mm ×100 mm); sealed with a rubber septum cap, sparged with nitrogen, and heated in a thermostatted oil bath preheated to the required temperature for varying lengths of time. Several sample films from each lot of powder were compression molded, cell attachment assays were conducted on a single 96-well plate, and a matrix of optical densities was obtained using the standard protocol described above.

TABLE 18

Optical Densities of Cell Attachment Assays

| | PnF [ppm] | Time [min] | Temp. [°C.] | N | OD [mean] | ± s | CV |
|---|---|---|---|---|---|---|---|
| Bare Plate | Solution coated with 100 μl of 1 μg-PnF/ml | | | 8 | 0.690 | ±0.050 | 7% |
| 103,082-A | 20 | 1/4 | 150° | 8 | 0.691 | ±0.035 | 5% |
| 103,082-B | 20 | 5 | 150° | 7 | 0.610 | ±0.083 | 14% |
| 103,082-C | 20 | 40 | 150° | 7 | 0.554 | ±0.038 | 7% |
| 103,082-D | 20 | 10 | 165° | 7 | 0.561 | ±0.064 | 11% |
| 103,082-E | 20 | 5 | 180° | 7 | 0.517 | ±0.070 | 14% |
| 103,082-F | 20 | 20 | 180° | 5 | 0.330 | ±0.143 | 43% |
| 103,082-G | 20 | 10 | 195° | 7 | 0.364 | ±0.118 | 32% |
| 103,082-H | 20 | 40 | 195° | 8 | 0.204 | ±0.072 | 35% |
| 103,082-I | 20 | 5 | 210° | 6 | 0.348 | ±0.080 | 23% |
| 103,082-J | 20 | 10 | 210° | 6 | 0.205 | ±0.077 | 36% |
| 103,082-K | 20 | 20 | 210° | 8 | 0.106 | ±0.079 | 75% |

The performance of the compression molded disks of polystyrene in the cell attachment assay decreased with increasing time and with increasing temperature in a complex manner. These data confirmed that exchange of ProNectin®F on the surface of the polystyrene powder conferred stabilization towards thermal deactivation during the thermal challenge.

The time-temperature experiments represent a response surface which was fitted by multivariate regression analysis. A model was defined which assumed a semi-first order reaction for thermal degradation with the rate constant being exponential in temperature. The fit of this second equation is $R^2$ =0.969, and has the satisfying property of fitting only three adjustable parameters to the 11 data points. The following parameters added together to form an equation which can be used to interpolate between points on the time-temperature response surface.

Parameter estimates for Ln[Ln[$A_0$/A)] $R^2$ = 0.969 Calcium stabilized.

| Term | Coefficient | Std Error | t Ratio | Prob > \|t\| |
|---|---|---|---|---|
| Intercept | 11.878449 | 1.22902 | 9.66 | 0.0000 |
| Ln t | 0.3219709 | 0.04650 | 6.92 | 0.0001 |
| 1/°K. | −6009.332 | 539.389 | −11.14 | 0.0000 |

EXAMPLE 3.

Preferred Embodiments of Coating Process.

The objective of most of the experimentation described herein has been to make a mixture of polystyrene and ProNectin®F and fabricate it into plasticware useful in tissue culture applications. The fabrication method to be used is injection molding. The injection molding process is characterized by parameters of time, temperature, and mechanical shear stress; all of which determine the activity of the ProNectin®F at the end of the fabrication process.

Compression molding may be used as a general method for fabricating plastics into sheets. Compression molding is easier to carry out on a laboratory scale than injection molding. Compression molding combined with the thermal stress experiments was used to model the time and temperature parameters of the injection molding process. The mechanical shear stress parameter can not be readily modeled anywhere except in an actual injection molding experiment.

Compression molding experiments were used to determine how best to mix ProNectin®F with polystyrene. The performance of the best candidate mixture was validated for tolerance to shear stress in an actual injection molding experiment described below.

Grade of Polystyrene

The preferred embodiment uses a grade of polystyrene which contains no mold release agents, lubricants, or viscosity modifiers. Amoco is a major manufacturer of polystyrene. The IR3-C0 grade contains no additives. The GR3-C7 grade contains a mix of additives which are commonly specified for injection molding applications. The detrimental effects of the presence of such additives is shown in the section entitled "Effects of Additives in the Polystyrene", and is summarized below:

TABLE 19

Effect of Additives in the Polystyrene.

| Sample | PnF [ppm] | Polymer Disks | N | OD [mean] | ± s | CV |
|---|---|---|---|---|---|---|
| Bare Plate | Solution coated 1 μg-PnF/ml | | 8 | 0.797 | ±0.037 | 5% |
| 102,028-2 | 200 | PS [Amoco IR3-C0] | 8 | 0.557 | ±0.046 | 8% |
| 102,028-10 | 200 | PS [Amoco GR3-C7 | 8 | 0.106 | ±0.117 | 111% |

Particle Size Of Polystyrene

ProNectin®F will attach to the exposed surface of polystyrene particles. The goal is to achieve an appropriate ratio of μg-PnF per g-PS. One parameter which defines the absolute amount of ProNectin®F which attaches to the polystyrene is the surface area of the polystyrene particles. Small particles possess a greater surface to volume ratio. In general, the use of smaller particles favors absorbing more ProNectin®F per gram of polystyrene. However, it is more difficult to make smaller particles. The preferred embodiment uses polystyrene ground to pass a 20 mesh sieve (>20 mesh). This choice is supported by the relative insensitivity of performance to mesh size over the range of 20 mesh to >100 mesh as shown in the section entitled "Effect of Deposition Methods and Mesh Size", and is summarized below:

TABLE 20

Effect of Deposition Method & Mesh Size

| Sample | PnF [ppm] | Deposition Method | PS Powder mesh range | N | OD [mean] | ± s | CV |
|---|---|---|---|---|---|---|---|
| Bare Plate | Solution coated with 100 μl of 1 μg-PnF/ml | | | 8 | 0.655 | ±0.099 | 15% |
| 103,065-C | 150 | Vortex Dil'n | >100 | 8 | 0.468 | ±0.112 | 24% |
| 103,065-F | 150 | Vortex Dil'n | 60–80 | 8 | 0.532 | ±0.071 | 13% |
| 103,065-I | 150 | Vortex Dil'n | 20–40 | 8 | 0.410 | ±0.043 | 10% |

Coating Methods

Evaporative Deposition

In evaporative deposition, a fixed amount of ProNectin®F is dissolved in formic acid solvent, polystyrene powder is added to the solvent, and the solvent is evaporated. All of the ProNectin®F is presumed to be deposited onto the polystyrene powder. A plot of cell attachment activity versus ProNectin®F concentration shows a plateau above 400 ppm. The results are shown in the section entitled "Deposition of ProNectin®F onto Polystyrene by Evaporative Coating", and is summarized below:

TABLE 21

Deposition of ProNectin ® F onto Polystyrene-by Evaporative Coating.

| | PnF [ppm] | PS Powder mesh range | N | OD [mean] | ± s | CV |
|---|---|---|---|---|---|---|
| Bare Plate | Solution coated with 100 μl of 1 μg-PnF/ml | | 8 | 0.573 | ±0.024 | 4% |
| 102-17-03 | 400 | >100 | 8 | 0.493 | ±0.069 | 14% |
| 103-64-A | 400 | >100 | 8 | 0.461 | ±0.045 | 10% |
| 103-64-B | 200 | >100 | 8 | 0.352 | ±0.086 | 24% |
| 103-64-C | 150 | >100 | 8 | 0.181 | ±0.055 | 30% |
| 103-64-D | 100 | >100 | 8 | 0.115 | ±0.056 | 49% |
| 103-64-E | 50 | >100 | 8 | 0.012 | ±0.049 | 408% |

Coating Methods

Vortex Deposition

In vortex deposition, a fixed amount of ProNectin®F is dissolved in formic acid solvent, polystyrene powder is added to the solvent, and a non-solvent is added under conditions of vigorous agitation (vortexing). ProNectin®F is deposited onto the polystyrene powder. Under some circumstances, this method may be the preferred embodiment because this method achieved high attachment activities using relatively smaller amounts of ProNectin®F in the coating mixture. A plot of cell attachment activity versus ProNectin®F concentration shows a plateau above 100 ppm. The results are shown in the section entitled "Deposition of ProNectin®F onto Polystyrene by Vortex Dilution Coating", and is summarized below:

TABLE 22

Deposition of ProNectin ® F onto Polystyrene by Vortex Dilution Coating.

| | PnF [ppm] | PS Powder mesh range | N | OD [mean] | ± s | CV |
|---|---|---|---|---|---|---|
| Bare Plate | Solution coated with 100 μl of 1 μg-PnF/ml | | 8 | 0.799 | ±0.026 | 3% |
| 103-66-00 | Solution coated with 100 μl of 1 μg-PnF/ml | | 8 | 0.747 | ±0.052 | 7% |
| 103-66-A | 300 | >20 | 8 | 0.516 | ±0.048 | 9% |
| 103-66-B | 250 | >20 | 8 | 0.641 | ±0.073 | 11% |
| 103-66-C | 200 | >20 | 8 | 0.627 | +0.068 | 11% |
| 103-66-D | 150 | >20 | 8 | 0.650 | ±0.057 | 9% |
| 103-66-E | 100 | >20 | 8 | 0.544 | ±0.067 | 12% |
| 103-66-F | 50 | >20 | 8 | 0.592 | ±0.060 | 10% |

Vortex deposition may be conducted using ProNectin®F dissolved in 85% formic acid, 10.0M aqueous urea, or 4.5 molar aqueous lithium perchlorate. Dissolution in aqueous urea is the preferred embodiment in the case of vortex dilution because urea is the least toxic or corrosive reagent of this group. These results are shown in the section entitled "Lot Reproducibility & Rinses with Calcium Salts", and are summarized below:

TABLE 23

Lot Reproducibilities and Rinses with Calcium Salts.

| | Comments | Time [min] | Temp [°C.] | N | OD [mean] | ± s | CV |
|---|---|---|---|---|---|---|---|
| Bare Plate | Solution coated with 100 μl of 1 μg-PnF-/ml | | | 8 | 0.491 | ±0.041 | 1% |
| 103,080-H | Lot #26; Formic; Water Rinse | 1/4 | 150° | 7 | 0.361 | ±0.132 | 32% |
| 103,080-I | Lot #26; Formic; $CaCl_2$ Rinse | 1/4 | 150° | 8 | 0.494 | ±0.043 | 13% |
| 103,080-J | Lot #26; Urea; $CaCl_2$ Rinse | 1/4 | 150° | 8 | 0.548 | ±0.036 | 22% |
| 103,080-K | Lot #26; $LiClO_4$; $CaCl_2$ Rinse | 1/4 | 150° | 8 | 0.519 | ±0.059 | 15% |

This list of solvent systems is not exhaustive. Other chaotropic reagents may be used to dissolve ProNectin®F in aqueous solutions. Other organic liquids may be used to dissolve the ProNectin®F. Other organic liquids may be used as non-solvents.

Coating Methods

Stirred Deposition

In stirred deposition, ProNectin®F is initially dissolved at "high" concentration (~1 mg/ml) in a suitable solvent. The preferred solvent is 10.0M urea. A working solution for coating is prepared by diluting the concentrate down to 5–50 μg/ml into 150 mmolar aqueous sodium chloride solution. Coating of the polystyrene is conducted by adding the powdered polystyrene to the working solution and stirring for 1 hour. Three variants were used, which differed in the way the polystyrene powder was prewetted before being added to the working solution. These results are shown in the section entitled "Calcium Stabilization of ProNectin®F", and are summarized below:

TABLE 24

Calcium Stabilization of ProNectin ® F.

| | Comments | Time [min] | Temp [°C.] | N | OD [mean] | ± s | CV |
|---|---|---|---|---|---|---|---|
| Bare Plate | Solution coated with 100 μl of 1 μg-PnF/ml | | | 8 | 0.549 | ±0.044 | 1% |
| 103,081-5A | Dry Powder | 1/4 | 150° | 8 | 0.519 | ±0.065 | 13% |
| 103,081-3A | Wetted 50% MeOH | 1/4 | 150° | 8 | 0.560 | ±0.062 | 11% |
| 103,081-1A | Wetted 100% MeOH | 1/4 | 150° | 8 | 0.531 | ±0.094 | 18% |
| 103,081-5B | Dry Powder | 5 | 200° | 8 | 0.172 | ±0.037 | 22% |
| 103,081-6B | Dry Powder, Ca+2 | 5 | 200° | 8 | 0.418 | ±0.064 | 15% |
| 103,081-4B | Wetted 50% MeOH; Ca+2 | 5 | 200° | 7 | 0.311 | ±0.099 | 32% |
| 103,081-2B | Wetted 100% MeOH; Ca+2 | 5 | 200° | 7 | 0.194 | ±0.052 | 27% |

Based on the results from compression moldings, the preferred embodiment is to use the dry polystyrene powder because this method is easiest to do. The rational for using dry powder becomes much more compelling when the results from thermal stress and calcium stabilization are considered. In these cases, preparations made using dry powdered polystyrene provide superior performance.

Of the three methods for depositing ProNectin®F onto polystyrene powders, the stirred deposition method is the preferred embodiment. It is the most readily scaled to handling larger quantities of polystyrene.

During the process of stirred deposition, the concentration of ProNectin®F in the working solution determines the amount deposited onto the surface of the polystyrene powder. In order to characterize this deposition phenomenon, we measured the deposition of ProNectin®F onto flat sheets of polystyrene with known surface areas. These results are shown in the section entitled "Relationship of Solution Concentrations to Surface Deposition".

The preferred embodiment is to work at concentrations in the range of 5–50 μg-PnF/ml. The most preferred embodiment is to work at 10–20 μg-PnF/ml. Other concentrations may become preferred for reasons relating coating costs to the cell attachment performance of the final plasticware products.

Using the techniques for the Fluorescamine assay described above, ProNectin®F actually deposited onto polystyrene powders was quantitated. Preparation of compression molded film samples and a cell attachment assay were conducted using standard protocols described above. The results of the assay are shown in Table 25.

TABLE 25

Stirred Deposition of ProNectin ® F onto Polystyrene Powders.

| | PnF [μg/ml] Solution | PnF [μg/cm$^2$] Surface | Time [min] | Temp. [°C.] | N | OD [mean] | ± s | CV |
|---|---|---|---|---|---|---|---|---|
| Bare Plate | Solution coated with 100 μl of 1 μg-PnF/ml | | | | 8 | 0.627 | ±0.014 | 2% |
| 103-083-A1 | 40 | 35.6 | 1/4 | 150° | 8 | 0.615 | ±0.019 | 3% |
| 103-083-B1 | 20 | 26.1 | 1/4 | 150° | 8 | 0.599 | ±0.040 | 7% |
| 103-083-C1 | 10 | n/d | 1/4 | 150° | 8 | 0.602 | ±0.021 | 3% |
| 103-083-D1 | 5 | 18.6 | 1/4 | 150° | 8 | 0.531 | ±0.039 | 7% |

Based on these results, the preferred embodiment is to coat polystyrene from a solution concentration of 10–20 μg/ml.

Stabilized ProNectin®F

The results of thermal stress experiments are shown in the section entitled "Thermal Stress Matrix for Unstabilized ProNectinF". The first indication that it is possible to intervene in the thermal deactivation process was observed in the experiments shown in the section entitled "Lot Reproducibility & Rinses with Calcium Salts", as summarized below:

TABLE 26

Lot Reproducibilities & Rinses with Calcium Salts.

| | Comments | Time [min] | Temp [°C.] | N | OD [mean] | ± s | CV |
|---|---|---|---|---|---|---|---|
| Bare Plate | Solution coated with 100 μl of 1 μg-PnF/ml | | | 8 | 0.491 | ±0.041 | 1% |
| 103,080-H | Lot #26; Formic: Water Rinse | 1/4 | 150° | 7 | 0.361 | ±0.132 | 32% |
| 103,080-I | Lot #26; Formic: $CaCl_2$ Rinse | 1/4 | 150° | 8 | 0.494 | ±0.043 | 13% |

In this experiment, no thermal stress other than that resulting from the compression molding was encountered. The sample which was rinsed with calcium chloride solution performed significantly better than the sample rinsed with water.

The first demonstration that it is possible to intervene in the thermal deactivation process under more severe conditions was observed in the experiments shown in the section entitled "Calcium Stabilization of ProNectin®F", as summarized below:

TABLE 27

Calcium Stabilization of ProNectin ® F.

| | Comments | Time [min] | Temp [°C.] | N | OD [mean] | ± s | CV |
|---|---|---|---|---|---|---|---|
| Bare Plate | Solutuion coated with 100 μl of 1 μg-PnF/ml | | | 8 | 0.549 | ±0.044 | 1% |
| 103,081-5B | Dry Powder | 5 | 200° | 8 | 0.172 | ±0.037 | 22% |
| 103,081-6B | Dry Powder; $Ca^{+2}$ Rinse | 5 | 200° | 8 | 0.418 | ±0.064 | 15% |

The calcium chloride solutions were prepared from calcium chloride desiccant which contains titratable base in the amount of 0.006 meq. The presence of the titratable base leads to slightly elevated pH's. The preferred embodiment is to conduct the rinse with calcium chloride solution in two stages: 100 mM $CaCl_2$ followed by 10 mM $CaCl_2$, although in some cases, 1 mM $CaSO_4$ may be substituted for the 10 mM $CaCl_2$ or may be used alone.

The extent to which ProNectin®F may be stabilized towards thermal deactivation is shown in the section entitled "Thermal Stress Matrix for Calcium Stabilized ProNectin®F".

The data points in Table 18 were subjected to multivariate regression analysis, and a equation was derived for predicting deactivation as a function of time and temperature. The general form of this equation was a semi-first order decay with the rate constant exponential in temperature.

The effects of calcium stabilization are apparent when compared against the data in Table 13. Comparing the fitting equations for the calcium stabilized and the non-stabilized cases was instructive. The coefficient on the 1/K° term was interpretable as the energy, $E_a/R$, of the thermal decomposition reaction, with $E_a$ =~12 Kcal/mole. Surprisingly, this activation energy does not change, within the confidence intervals, between the two response surfaces. What does change is a decrease in the pre-exponential frequency term Ln[A].

The coefficient on the term in time also changes. The interpretation of this last effect was not clear. It may be related to a surface diffusion phenomenon. In any case, the equations which predict cell culture performance as a function of time and temperature during the thermal challenge are of the form:

$$\mathrm{Ln}\left\{ \mathrm{Ln}\left(\frac{I_o}{I}\right) \right\} = \mathrm{Ln}(A) + b * \mathrm{Ln}(t) + \frac{E_a}{RT}$$

$$\mathrm{Ln}\left[\frac{I}{I_o}\right] = -A * \left(e^{\frac{E_a}{RT}}\right) * t^b$$

$$\frac{I}{I_o} = e^{-A*\left(e^{\frac{Ea}{RT}}\right)*t^b}$$

Where the coefficients have the values:

| | Calcium Stabilized | | Non-Stabilized | |
|---|---|---|---|---|
| Terms | Coefficient | Std Error | Coefficient | Std Error |
| Ln[A] | 11.8784 | ±1.2290 | 12.2560 | ±1.4924 |
| b | 0.32197 | ±0.04650 | 0.70493 | ±0.08461 |
| Ea | −11,933 | ±1070 | −12,767 | ±1337 |
| R2 | | 0.969 | 0.963 | |

The significance of calcium stabilization is that we now have a larger time-temperature window through which to conduct the thermomolding operation. The requirements for the time-temperature window are defined by the characteristics of the thermomolding process itself. For instance, in the case of injection molding, time is defined by the ratio between the contained volumes within the heated barrel of the screw extruder and within the mold, and by the cycle time on the mold, while temperature is defined by the nature of the plastic and the complexity of the mold. Together, these process parameters define "how long" and "how hot" the polypeptide will be stressed.

The preferred embodiment is to ion exchange the ProNectin®F on the surface of the polystyrene with calcium ion at slightly elevated pH, pH 8.6. Other combinations of multivalent metal cations and pH may serve to confer thermal stabilization. Calcium was chosen because it is commonly found in tissue culture media. A small increment of calcium leaching into the tissue culture media from the plasticware activated with ProNectin®F would constitute only a minimum perturbation on the function of the tissue culture media. Other metal ions which might be useful for stabilization are zinc and magnesium. Trivalent ions such as aluminum may also be useful.

Shear Stress Testing

Native polystyrene pellets (Amoco IR3-C0) were ground to a powder using an 8" vertical grinder and screened to a nominal size of >35 mesh with oversize particles being returned for regrinding. The measured mesh size distribution which was obtained is: (mesh,wt%)<30, 0.2%; 30–35, 11.3%; 35–40, 15.9%; 40–60, 44.9%; 60–80, 18.4%; 80–100, 5.9%; & >100, 3.4%. The polystyrene powder (2000 g) was slurried in 3500 ml of isopropanol for 5 minutes, filtered on a Buchner funnel, washed on the filter with an additional 2000 ml of isopropanol, sucked as dry as possible, and dried in air under ambient conditions.

ProNectin®F (500 mg) was dissolved in 500 ml of 10.0M aqueous urea solution to yield the stock solution of 1 mg/ml concentration. Aqueous saline (150 mM) was prepared by dissolving by sodium chloride (86.5 g) in 10.0 liters of deionized water. The saline solution was agitated using a mechanical stirrer (Lightning model L1UO8P) set at 1025 rpm, the power at 5.8 watts, and the pumping capacity at 365 L/min., with an impeller (model A-310) at the end of the shaft which was angled at 65° to the surface of the solution. Stock ProNectin®F solution (100 ml) was added dropwise over about 3 minutes to the stirred saline to give a final concentration of ProNectin®F of 10 μg/ml. To this solution was added 500 g of the ground, washed and dried polystyrene powder >35 mesh. The slurry was allowed to stir for 1 hour at ambient temperature. The polystyrene powder was recovered using a 26 cm Buchner funnel with a stationary porous filter (70 microns). After being sucked as dry as possible, the polystyrene powder was slurried on the funnel with 2 L of 1 mM calcium sulfate solution and again sucked dry. This treatment was repeated twice more. During the final filtration, the filter cake was compacted under an elastic dam. The recovered polystyrene powder was spread into a layer about 3 cm deep and dried for 15 hours in a forced draft oven at 40° C. This oven dried polystyrene powder (750 g) was loaded into a 2000 ml lyophilizer tube, connected to a vacuum line fitted with a trap cooled in liquid nitrogen, and evacuated to 0.008 Torr at 25° C. for 1 hour to achieve final drying. The vacuum line was back filled with dry nitrogen to ambient pressure. The lyophilizer tube was removed from the vacuum line, and its access port was sealed with a rubber stopper. The vacuum dried polystyrene powder was stored in these tubes until being poured into the feed hopper of the injection molding machine.

Injection molding using a 1.5 Kg sample of the polystyrene prepared above was conducted using a 5 ounce (141.8 g) TMC injection molding machine. The injection molding was conducted on a cycle time of 25 seconds. The mold used in this test was fashioned in a block of P20 semi-hardened tool steel with a disk shaped cavity of dimensions 1.188" diameter ×0.060" thickness using a 15° draft angle. The gate between the runner and the cavity was designed to exacerbate sheer stress effects and had dimensions of 0.040"× 0.060"×0.030" (height x width x length). A second mold cavity of completely arbitrary design was installed in the mold frame to increase the shot size to 61.5 grams so that the residence time in the barrel was approximately 58 seconds. The temperature profile on the barrel was: nozzle, 375° F.; front, 359° F.; middle, 360° F., and rear, 347° F.

Disks prepared in this manner from the coated polystyrene powder were optically indistinguishable from disks prepared from native polystyrene pellets (Amoco IR3-C0) as judged by the transparency of the disk portion of the mold. The sensitivity of the ProNectin®F to shear stresses inherent in the injection molding process was judged by regrinding samples of the molded objects and compression molding the reground polystyrene powder into films suitable for inclusion in the cell attachment assay described above. Shear stress is concentrated at the gate to the mold cavity. To judge this effect, samples for regrinding were taken from the runner immediately before the gate to the disk shaped cavity and from the disk shaped cavity. The results of these cell attachment assays are presented in Table 28.

TABLE 28

Shear Stress Testing During Injection Molding.

| | PnF [ppm] | Time | Temp | N | OD [mean] | ± s | CV |
|---|---|---|---|---|---|---|---|
| Bare Plate | Solution coated with 100 μl of 1 μg-PnF/ml | | | 8 | 0.396 | ±0.064 | 16% |
| 103,092-Z | 20 | 0.25 | 150° C. | 8 | 0.463 | ±0.059 | 13% |
| Reground Runner | 20 | 1.0 | 193° C. | 8 | 0.234 | ±0.075 | 32% |
| Reground Disk | 20 | 1.0 | 193° C. | 8 | 0.059 | ±0.027 | 46% |

The coated powder (103,092-Z) when compression molded in the form of a thin sheet performed equivalent to the solution coated bare plate in the cell attachment assay. The polystyrene which was recovered after the injection molding also showed activity in the cell attachment assay. Passage of the molten mixture of ProNectin®F and polystyrene through the gate into the disk shaped cavity led to a deterioration in cell attachment activity compared to the activity of the sample reground from the section of the runner immediately before the gate. This implicates shear stress as a mechanism for deactivating the ProNectin®F during the injection molding process. Shear stress can be alleviated through the design of the sprues, runners, gates, and cavities of the mold. The result of this experiment showed that ProNectin®F can undergo both thermal and mechanical stresses inherent in the injection molding process and retain its cell attachment function.

EXAMPLE 4.

Oligopeptide 92.10 and Attachment Assay

Peptide 92.10 was prepared to have the following sequence: (KKKM) $(GAGAGS)_2$ GAAVTGRGDSPASAAGY (GAGAGS) 2 (SEQ ID NO:21)

A known concentration of peptide 92.10 (estimated to be 41% pure by analytical hplc) and calcium sulfate was dissolved in 88% formic acid. Huntsman polystyrene polystyrene was loaded into a Buchner funnel and evacuated under a filter dam (Saran Wrap) to remove excess solution. The amount of entrained solution was determined gravimetrically before and after evaporation of formic acid solvent on a vacuum line. Powder samples were transferred from the Buchner funnel into 1 oz. wide mouth jars, and covered with a Kimwipe® tissue afixed with a rubber band. Multiple 1 oz. sample jars were loaded into a 1600 ml lyophilization tube and dried on a vacuum line fitted with a liquid nitrogen cooled trap to a final pressure of 4 m Torr with the samples at room temperature.

Several sample films from each lot of powder were compression molded from 250 mg of coated polystyrene between 304 stainless steel sheets using a Carver press with plattens heated electrically to 150° C. Four sample disks for cell attachment assay were taken from the center of each of three films using a standard 7 mm "one-hole-punch." All cell attachment assays were conducted on a single 96-well plate and optical densities obtained, as described above.

TABLE 29

Optical Densities of Cell Attachment Assays On Compression Molded PS With Peptide 92.10

| | Peptide 92.10 | Calcium | N | OD [mean] | ± s | CV |
|---|---|---|---|---|---|---|
| ProNectin ® F | 264 ppm | 5 ppm | 8 | 0.435 | ±0.071 | 16% |
| 126,031-A | 789 ppm | 25 ppm | 8 | 0.340 | ±0.094 | 28% |
| 126,031-B | 297 ppm | 15 ppm | 8 | 0.264 | ±0.054 | 20% |
| 126,031-C | 316 ppm | 32 ppm | 8 | 0.258 | ±0.083 | 32% |
| 126,031-D | 112 ppm | 23 ppm | 8 | 0.157 | ±0.079 | 50% |
| 126,031-E | 51 ppm | 21 ppm | 8 | 0.069 | ±0.043 | 62% |
| 126,031-F | 40 ppm | 33 ppm | 8 | 0.073 | ±0.070 | 96% |

TABLE 29-continued

Optical Densities of Cell Attachment Assays On Compression Molded PS With Peptide 92.10

| | Peptide 92.10 | Calcium | N | OD [mean] | ± s | CV |
|---|---|---|---|---|---|---|
| 126,031-G | 16 ppm | 27 ppm | 8 | 0.030 | ±0.031 | 100% |
| 126,031-H | 0 ppm | 26 ppm | 8 | 0.014 | ±0.027 | 190% |

Peptide 92.10 is clearly active in a compression molded format. It has about ¼ the activity (26% ±8%) of ProNectin®F on a weight basis. The specific activity can not be estimated without independently knowing the content of active RGD's.

EXAMPLE 5.

Chemical Modification of ProNectin F On the Surface Of An Injection Molded Polystyrene part To demonstrate the availability of ProNectin®F for chemical modification in thermoplastics comprising ProNectin®F, polystyrene with ProNectin®F was injection molded to form Petri dishes consisting of tops and bases. For this experiment, tops (sequence numbered 102, 060–160 and 102, 060–531) were taken and reacted with diazonium benzoylbiocytin (DBB). This reagent is specific for azo-coupling reactions with the tyrosine and histidine residues found in many proteins. Wilchek et al., Biochim. Biophys. Res. Comm., 138(2), 872–879 (1986). In the case of ProNectin®F, there exists a tyrosine residue in every repeating monomer unit, and there exists histidine residues in the head and tail sequences. For reaction with DBB, a solution of DBB reagent was added to each Petri top and permitted to stand for 10 minutes at room temperature. The solution of DBB reagent was prepared by diazotizing 0.50 mg of aminobenzoylbiocytin (Pierce #28023) with 1.0N hydrochloric acid (10.3 $\mu$L) and 0.112N sodium nitrite (10.3 $\mu$L) in an ice bath for 5 minutes. The reaction was stopped by adding 1.0N sodium hydroxide (8.8 $\mu$L) and was diluted to 50 mL with 100 mM borate buffer pH 9.0 containing 1.0 mg/mL of Pluronic F-68 surfactant (BASF). After coupling, the tops were rinsed with a stream of deionized water.

After azo-coupling of DBB to the tyrosine and histidine residues contained in the ProNectin®F exposed on the surface of the injection molded part, the physical location of the biotin moiety was visualized as follows. First, a blocking solution of hydroxypropylcellulose (HPC) was added to the Petri tops and permitted to stand for 5 minutes at room temperature. The blocking solution of HPC was prepared by diluting a stock solution at 50 mg/mL of hydroxypropylcellulose (Aldrich 19,188-4; MW 100,000) prepared in methanoVwater (1:1 v/v) to a final concentration of 1.0 mg/mL in deionized water. After blocking, the tops were rinsed with a stream of deionized water.

Second, streptavidin-horseradish peroxidase (Strpt-HRP) was immobilized to the biotin moiety of the DBB. To immobilize the Strpt-P, a solution of Strpt-HRP was added to the Petri tops and permitted to stand for 20 minutes at room temperature. The solution of streptavidin-horseradish peroxidase was prepared by diluting a stock solution of Strpt-HRP (Amersham #RPN 1231) 1000:1 into deionized water. After coupling with Strpt-HRP, the tops were rinsed in a stream of deionized water.

Third, a solution of diaminobiphenyl (DAB) reagent was added to the Petri tops and permitted to stand for 5 minutes at room temperature. The DAB reagent (Pierce #34065) was prepared in accordance with the manufacturer's instructions from 1.0 mL of DAB concentrate and 9.0 mL of buffered hydrogen peroxide. The immobilized horseradish peroxidase oxidized the DAB to an insoluble precipitate. After DAB enhancement, the tops were rinsed in a stream of deionized water.

To visualize the insoluble substrate, the precipitate of oxidized DAB was exposed to an aqueous gold sol and then developed with a silver(I)-hydroquinone stain. To expose the precipitate to the aqueous gold sol, a colloidal gold-sol (BioRad #170-6527) was added to the Petri tops and permitted to stand for 10 minutes at room temperature. After gold activation, the tops were rinsed in a stream of deionized water. To develop the gold sol exposed precipitate, a silver stain was added to the Petri tops and permitted to stand for 5 minutes at room temperature while protected from light. The silver stain solution was prepared by adding 0.50 mL of a solution of silver lactate [11.0 mg/mL in a pH 3.7 citrate buffer: citric acid, 27.0 g, and trisodium citrate, 22.0 g, diluted to 1000 mL with deionized water] to a solution of hydroquinone (43 mg) in 9.5 mL of the same citrate buffer pH 3.7. After silver staining, the tops were rinsed in a stream of deionized water and dried in air.

In this manner, a pattern of gray whorls and swirls was visualized on the surface of the injection molded part. The observed pattern of gray whorls and swirls is analogous to the pattern of blue whorls and swirls resulting from conducting attachment of VERO cells to the same surface and staining the cells with amidoblack.

The compositions and methods disclosed herein reduce the need for solution coating of finished plastic surfaces. The inventions offer substantial improvement over previously used methods for providing surfaces activated with proteins by allowing any molded device to be activated with one or more thermostable proteins simultaneous with the thermomolding process. This single step reduces costs associated with secondary manufacturing processes for deposition of proteins on the surface of thermomolded articles, many of which are solvent based, and provides the ability to produce finished goods at lower unit cost than conventional methods allow. Furthermore, the disclosed compositions and methods provide for the incorporation of thermostable proteins into devices whose shapes (e.g. spherical or otherwise three-dimensional) are not readily amenable to solution coating processes.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A composition comprising a functional thermostable polypeptide interdispersed within a thermoplastic resulting from a melt at a temperature of at least 60° C., wherein said polypeptide comprises repeating units from elastin, collagen, keratin or silk proteins, and a sequence intervening said repeating units, wherein said intervening sequence has at least one chemically active amino acid or a naturally occurring sequence having binding specificity for a protein receptor.

2. The composition of claim 1 wherein said polypeptide is from 3 to about 60 amino acids in length.

3. The composition of claim 1 wherein said polypeptide has a molecular weight of at least 25kD.

4. The composition of claim 1 wherein said intervening sequence comprises RGD.

5. The composition of claim 1 wherein said protein polymer is ProNectin®F (SLPF) or SLPL3.0.

6. The composition of claim 1 wherein said thermoplastic is polystyrene, polyethylene, polypropylene, or polymethylmethacrylate.

7. The composition of claim 1 further comprising a polypeptide thermostability enhancing additive.

8. A formed object produced by contacting a thermoplastic with a functional thermostable polypeptide, heating said thermoplastic and said polypeptide to at least 60° C. for at least 15 seconds to create a melt, molding said melt to form a functional thermostable polypeptide interdispersed within said thermoplastic, wherein said polypeptide comprises repeating units from elastin, collagen, keratin or silk proteins, and a sequence intervening said repeating units, said intervening sequence having at least one chemically active amino acid or a naturally occurring sequence having binding specificity for a protein receptor.

9. A method for producing a functional thermostable polypeptide interdispersed within a thermoplastic, said method comprising:

forming a mixture of thermoplastic and said functional thermostable polypeptide, heating said thermoplastic and said polypeptide to create a melt, molding said melt into a predetermined form, whereby a functional thermostable polypeptide is interdispersed within said thermoplastic, wherein said polypeptide comprises repeating units from elastin, collagen, keratin or silk proteins, and a sequence intervening said repeating units, said intervening sequence having at least one chemically active amino acid or a naturally occurring sequence having binding specificity for a protein receptor.

10. A method for producing functional ProNectin®F (SLPF) interdispersed within a thermoplastic, said method comprising:

forming a mixture of a thermoplastic and functional ProNectin®F (SLPF), heating said thermoplastic and said ProNectin®F (SLPF) to create a melt, molding said melt into a predetermined form, whereby functional ProNectin®F (SLPF) is interdispersed within said thermoplastic.

* * * * *

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
( A ) LENGTH: 44 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:1:

```
Lys Lys Met Gly Ala Gly Ala Gly Ser Gly Ala Gly Ala Gly Ser Gly
1               5                   10                  15

Ala Ala Val Thr Gly Arg Gly Asp Ser Pro Ala Ser Ala Ala Gly Tyr
            20                  25                  30

Gly Ala Gly Ala Gly Ser Gly Ala Gly Ala Gly Ser
        35                  40
```

( 2 ) INFORMATION FOR SEQ ID NO:2:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:2:

```
Arg Glu Asp Val
1
```

( 2 ) INFORMATION FOR SEQ ID NO:3:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:3:

```
Tyr Ile Gly Ser Arg
1               5
```

( 2 ) INFORMATION FOR SEQ ID NO:4:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:4:

```
Gly Ala Gly Cys
1
```

( 2 ) INFORMATION FOR SEQ ID NO:5:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:5:

Gly Cys Cys Val
1

( 2 ) INFORMATION FOR SEQ ID NO:6:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:6:

Val Ser Pro Asp
1

( 2 ) INFORMATION FOR SEQ ID NO:7:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:7:

Val Cys Pro Asp
1

( 2 ) INFORMATION FOR SEQ ID NO:8:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:8:

Asp Pro Gly Lys
1

( 2 ) INFORMATION FOR SEQ ID NO:9:

( i ) SEQUENCE CHARACTERISTICS:
( A ) LENGTH: 45 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "0ligonucleotide"

( x i ) SEQUENCE DESCRIPTION: SEQ ID NO:9:

CGCTACGTAG TTCTGCCACG TCCGGTATGT TTCGAAAAAG CTGCA 45

( 2 ) INFORMATION FOR SEQ ID NO:10:

( i ) SEQUENCE CHARACTERISTICS:
( A ) LENGTH: 45 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "Oligonucleotide"

( x i ) SEQUENCE DESCRIPTION: SEQ ID NO:10:

GCTTTTTCGA AACATACCGG ACGTGGCAGA ACTACGTAGC GTGCA 45

( 2 ) INFORMATION FOR SEQ ID NO:11:

( i ) SEQUENCE CHARACTERISTICS:
( A ) LENGTH: 222 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:11:

GGTGCCGGCA GCGGTGCAGG AGCCGGTTCT GGAGCTGGCG CGGGCTCTGG CGCGGGCGCA 60

GGATCCGGCG CAGGCGCTGG TTCTGGCGCA GGGGCAGGCT CTGGCGCAGG AGCGGGGTCT 120

GGAGCTGCAC GCTACGTAGT TCTGCCACGT CCGGTATGTT TCGAAAAAGC TGCAGGCTAT 180

GGAGCTGGCG CTGGCTCAGG TGCTGGAGCA GGAAGCGGAG CG 222

( 2 ) INFORMATION FOR SEQ ID NO:12:

( i ) SEQUENCE CHARACTERISTICS:
( A ) LENGTH: 74 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:12:

Gly Ala Gly Ser Gly Ala Gly Ala Gly Ser Gly Ala Gly Ala Gly Ser
1 5 10 15

Gly Ala Gly Ala Gly Ser Gly Ala Gly Ala Gly Ser Gly Ala Gly Ala
20 25 30

Gly Ser Gly Ala Gly Ala Gly Ser Gly Ala Ala Arg Tyr Val Val Leu
35 40 45

Pro Arg Pro Val Cys Phe Glu Lys Ala Ala Gly Tyr Gly Ala Gly Ala
50 55 60

Gly Ser Gly Ala Gly Ala Gly Ser Gly Ala
65 70

( 2 ) INFORMATION FOR SEQ ID NO:13:

( i ) SEQUENCE CHARACTERISTICS:
( A ) LENGTH: 945 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:13:

Met Asp Pro Val Val Leu Gln Arg Arg Asp Trp Glu Asn Pro Gly Val
1 5 10 15

Thr Gln Leu Asn Arg Leu Ala Ala His Pro Pro Phe Ala Ser Asp Pro
20 25 30

-continued

Met Gly Ala Gly Ser Gly Ala Gly Ala Gly Ser Gly Ala Gly Ala Gly
35 40 45

Ser Gly Ala Gly Ala Gly Ser Gly Ala Gly Ala Gly Ser Gly Ala Gly
50 55 60

Ala Gly Ser Gly Ala Gly Ala Gly Ser Gly Ala Ala Arg Tyr Val Val
65 70 75 80

Leu Pro Arg Pro Val Cys Phe Glu Lys Ala Ala Gly Tyr Gly Ala Gly
85 90 95

Ala Gly Ser Gly Ala Gly Ala Gly Ser Gly Ala Gly Ala Gly Ser Gly
100 105 110

Ala Gly Ala Gly Ser Gly Ala Gly Ala Gly Ser Gly Ala Gly Ala Gly
115 120 125

Ser Gly Ala Gly Ala Gly Ser Gly Ala Gly Ala Gly Ser Gly Ala Gly
130 135 140

Ala Gly Ser Gly Ala Ala Arg Tyr Val Val Leu Pro Arg Pro Val Cys
145 150 155 160

Phe Glu Lys Ala Ala Gly Tyr Gly Ala Gly Ala Gly Ser Gly Ala Gly
165 170 175

Ala Gly Ser Gly Ala Gly Ala Gly Ser Gly Ala Gly Ala Gly Ser Gly
180 185 190

Ala Gly Ala Gly Ser Gly Ala Gly Ala Gly Ser Gly Ala Gly Ala Gly
195 200 205

Ser Gly Ala Gly Ala Gly Ser Gly Ala Gly Ala Gly Ser Gly Ala Ala
210 215 220

Arg Tyr Val Val Leu Pro Arg Pro Val Cys Phe Glu Lys Ala Ala Gly
225 230 235 240

Tyr Gly Ala Gly Ala Gly Ser Gly Ala Gly Ala Gly Ser Gly Ala Gly
245 250 255

Ala Gly Ser Gly Ala Gly Ala Gly Ser Gly Ala Gly Ala Gly Ser Gly
260 265 270

Ala Gly Ala Gly Ser Gly Ala Gly Ala Gly Ser Gly Ala Gly Ala Gly
275 280 285

Ser Gly Ala Gly Ala Gly Ser Gly Ala Ala Arg Tyr Val Val Leu Pro
290 295 300

Arg Pro Val Cys Phe Glu Lys Ala Ala Gly Tyr Gly Ala Gly Ala Gly
305 310 315 320

Ser Gly Ala Gly Ala Gly Ser Gly Ala Gly Ala Gly Ser Gly Ala Gly
325 330 335

Ala Gly Ser Gly Ala Gly Ala Gly Ser Gly Ala Gly Ala Gly Ser Gly
340 345 350

Ala Gly Ala Gly Ser Gly Ala Gly Ala Gly Ser Gly Ala Gly Ala Gly
355 360 365

Ser Gly Ala Ala Arg Tyr Val Val Leu Pro Arg Pro Val Cys Phe Glu
370 375 380

Lys Ala Ala Gly Tyr Gly Ala Gly Ala Gly Ser Gly Ala Gly Ala Gly
385 390 395 400

Ser Gly Ala Gly Ala Gly Ser Gly Ala Gly Ala Gly Ser Gly Ala Gly
405 410 415

Ala Gly Ser Gly Ala Gly Ala Gly Ser Gly Ala Gly Ala Gly Ser Gly
420 425 430

Ala Gly Ala Gly Ser Gly Ala Gly Ala Gly Ser Gly Ala Ala Arg Tyr
435 440 445

Val Val Leu Pro Arg Pro Val Cys Phe Glu Lys Ala Ala Gly Tyr Gly 450 455 460

Ala Gly Ala Gly Ser Gly Ala Gly Ala Gly Ser Gly Ala Gly Ala Gly
465 470 475 480

Ser Gly Ala Gly Ala Gly Ser Gly Ala Gly Ala Gly Ser Gly Ala Gly
485 490 495

Ala Gly Ser Gly Ala Gly Ala Gly Ser Gly Ala Gly Ala Gly Ser Gly
500 505 510

Ala Gly Ala Gly Ser Gly Ala Ala Arg Tyr Val Val Leu Pro Arg Pro
515 520 525

Val Cys Phe Glu Lys Ala Ala Gly Tyr Gly Ala Gly Ala Gly Ser Gly
530 535 540

Ala Gly Ala Gly Ser Gly Ala Gly Ala Gly Ser Gly Ala Gly Ala Gly
545 550 555 560

Ser Gly Ala Gly Ala Gly Ser Gly Ala Gly Ala Gly Ser Gly Ala Gly
565 570 575

Ala Gly Ser Gly Ala Gly Ala Gly Ser Gly Ala Gly Ala Gly Ser Gly
580 585 590

Ala Ala Arg Tyr Val Val Leu Pro Arg Pro Val Cys Phe Glu Lys Ala
595 600 605

Ala Gly Tyr Gly Ala Gly Ala Gly Ser Gly Ala Gly Ala Gly Ser Gly
610 615 620

Ala Gly Ala Gly Ser Gly Ala Gly Ala Gly Ser Gly Ala Gly Ala Gly
625 630 635 640

Ser Gly Ala Gly Ala Gly Ser Gly Ala Gly Ala Gly Ser Gly Ala Gly
645 650 655

Ala Gly Ser Gly Ala Gly Ala Gly Ser Gly Ala Ala Arg Tyr Val Val
660 665 670

Leu Pro Arg Pro Val Cys Phe Glu Lys Ala Ala Gly Tyr Gly Ala Gly
675 680 685

Ala Gly Ser Gly Ala Gly Ala Gly Ser Gly Ala Gly Ala Gly Ser Gly
690 695 700

Ala Gly Ala Gly Ser Gly Ala Gly Ala Gly Ser Gly Ala Gly Ala Gly
705 710 715 720

Ser Gly Ala Gly Ala Gly Ser Gly Ala Gly Ala Gly Ser Gly Ala Gly
725 730 735

Ala Gly Ser Gly Ala Ala Arg Tyr Val Val Leu Pro Arg Pro Val Cys
740 745 750

Phe Glu Lys Ala Ala Gly Tyr Gly Ala Gly Ala Gly Ser Gly Ala Gly
755 760 765

Ala Gly Ser Gly Ala Gly Ala Gly Ser Gly Ala Gly Ala Gly Ser Gly
770 775 780

Ala Gly Ala Gly Ser Gly Ala Gly Ala Gly Ser Gly Ala Gly Ala Gly
785 790 795 800

Ser Gly Ala Gly Ala Gly Ser Gly Ala Gly Ala Gly Ser Gly Ala Ala
805 810 815

Arg Tyr Val Val Leu Pro Arg Pro Val Cys Phe Glu Lys Ala Ala Gly
820 825 830

Tyr Gly Ala Gly Ala Gly Ser Gly Ala Gly Ala Gly Ser Gly Ala Gly
835 840 845

Ala Gly Ser Gly Ala Gly Ala Gly Ser Gly Ala Gly Ala Gly Ser Gly
850 855 860

Ala Gly Ala Gly Ser Gly Ala Gly Ala Gly Ser Gly Ala Gly Ala Gly
865 870 875 880

-continued

Ser Gly Ala Gly Ala Gly Ser Gly Ala Ala Arg Tyr Val Val Leu Pro
885 890 895

Arg Pro Val Cys Phe Glu Lys Ala Ala Gly Tyr Gly Ala Gly Ala Gly
900 905 910

Ser Gly Ala Gly Ala Gly Ser Gly Ala Gly Ala Met Asp Pro Gly Arg
915 920 925

Tyr Gln Leu Ser Ala Gly Arg Tyr His Tyr Gln Leu Val Trp Cys Gln
930 935 940

Lys
945

( 2 ) INFORMATION FOR SEQ ID NO:14:

( i ) SEQUENCE CHARACTERISTICS:
( A ) LENGTH: 45 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "oligopeptide"

( x i ) SEQUENCE DESCRIPTION: SEQ ID NO:14:

CCGGGTGCAT CGATCAAAGT AGCTGTTAGC GCCGGACCGT CTGCA 45

( 2 ) INFORMATION FOR SEQ ID NO:15:

( i ) SEQUENCE CHARACTERISTICS:
( A ) LENGTH: 45 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "oligonucleotide"

( x i ) SEQUENCE DESCRIPTION: SEQ ID NO:15:

GACGGTCCGG CGCTAACAGC TACTTTGATC GATGCACCCG GTGCA 45

( 2 ) INFORMATION FOR SEQ ID NO:16:

( i ) SEQUENCE CHARACTERISTICS:
( A ) LENGTH: 228 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:16:

GGTGCCGGCA GCGGTGCAGG AGCCGGTTCT GGAGCTGGCG CGGGCTCTGG CGCGGGCGCA 60

GGATCCGGCG CAGGCGCTGG TTCTGGCGCA GGGGCAGGCT CTGGCGCAGG AGCGGGGTCT 120

GGAGCTGCAC CGGGTGCATC GATCAAAGTA GCTGTTAGCG CCGGACCGTC TGCAGGCTAT 180

GGAGCTGGCG CTGGCTCAGG TGCTGGAGCA GGAAGCGGAG CGGGTGCC 228

( 2 ) INFORMATION FOR SEQ ID NO:17:

( i ) SEQUENCE CHARACTERISTICS:
( A ) LENGTH: 76 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:17:

-continued

```
Gly Ala Gly Ser Gly Ala Gly Ala Gly Ser Gly Ala Gly Ala Gly Ser
1               5                   10                  15

Gly Ala Gly Ala Gly Ser Gly Ala Gly Ala Gly Ser Gly Ala Gly Ala
            20                  25                  30

Gly Ser Gly Ala Gly Ala Gly Ser Gly Ala Ala Pro Gly Ala Ser Ile
        35                  40                  45

Lys Val Ala Val Ser Ala Gly Pro Ser Ala Gly Tyr Gly Ala Gly Ala
    50                  55                  60

Gly Ser Gly Ala Gly Ala Gly Ser Gly Ala Gly Ala
65                  70                  75
```

( 2 ) INFORMATION FOR SEQ ID NO:18:

( i ) SEQUENCE CHARACTERISTICS:
( A ) LENGTH: 1018 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:18:

```
Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met Gly Ala Gly Ser Gly Ala Gly Ala Gly Ser Gly Ala Gly Ala Gly
        35                  40                  45

Ser Gly Ala Gly Ala Gly Ser Gly Ala Gly Ala Gly Ser Gly Ala Gly
    50                  55                  60

Ala Gly Ser Gly Ala Gly Ala Gly Ser Gly Ala Ala Pro Gly Ala Ser
65                  70                  75                  80

Ile Lys Val Ala Val Ser Ala Gly Pro Ser Ala Gly Tyr Gly Ala Gly
                85                  90                  95

Ala Gly Ser Gly Ala Gly Ala Gly Ser Gly Ala Gly Ala Gly Ser Gly
            100                 105                 110

Ala Gly Ala Gly Ser Gly Ala Gly Ala Gly Ser Gly Ala Gly Ala Gly
        115                 120                 125

Ser Gly Ala Gly Ala Gly Ser Gly Ala Gly Ala Gly Ser Gly Ala Gly
    130                 135                 140

Ala Gly Ser Gly Ala Ala Pro Gly Ala Ser Ile Lys Val Ala Val Ser
145                 150                 155                 160

Ala Gly Pro Ser Ala Gly Tyr Gly Ala Gly Ala Gly Ser Gly Ala Gly
                165                 170                 175

Ala Gly Ser Gly Ala Gly Ala Gly Ser Gly Ala Gly Ala Gly Ser Gly
            180                 185                 190

Ala Gly Ala Gly Ser Gly Ala Gly Ala Gly Ser Gly Ala Gly Ala Gly
        195                 200                 205

Ser Gly Ala Gly Ala Gly Ser Gly Ala Gly Ala Gly Ser Gly Ala Ala
    210                 215                 220

Pro Gly Ala Ser Ile Lys Val Ala Val Ser Ala Gly Pro Ser Ala Gly
225                 230                 235                 240

Tyr Gly Ala Gly Ala Gly Ser Gly Ala Gly Ala Gly Ser Gly Ala Gly
                245                 250                 255

Ala Gly Ser Gly Ala Gly Ala Gly Ser Gly Ala Gly Ala Gly Ser Gly
            260                 265                 270
```

-continued

Ala Gly Ala Gly Ser Gly Ala Gly Ala Gly Ser Gly Ala Gly Ala Gly
275 280 285

Ser Gly Ala Gly Ala Gly Ser Gly Ala Ala Pro Gly Ala Ser Ile Lys
290 295 300

Val Ala Val Ser Ala Gly Pro Ser Ala Gly Tyr Gly Ala Gly Ala Gly
305 310 315 320

Ser Gly Ala Gly Ala Gly Ser Gly Ala Gly Ala Gly Ser Gly Ala Gly
325 330 335

Ala Gly Ser Gly Ala Gly Ala Gly Ser Gly Ala Gly Ala Gly Ser Gly
340 345 350

Ala Gly Ala Gly Ser Gly Ala Gly Ala Gly Ser Gly Ala Gly Ala Gly
355 360 365

Ser Gly Ala Ala Pro Gly Ala Ser Ile Lys Val Ala Val Ser Ala Gly
370 375 380

Pro Ser Ala Gly Tyr Gly Ala Gly Ala Gly Ser Gly Ala Gly Ala Gly
385 390 395 400

Ser Gly Ala Gly Ala Gly Ser Gly Ala Gly Ala Gly Ser Gly Ala Gly
405 410 415

Ala Gly Ser Gly Ala Gly Ala Gly Ser Gly Ala Gly Ala Gly Ser Gly
420 425 430

Ala Gly Ala Gly Ser Gly Ala Gly Ala Gly Ser Gly Ala Ala Pro Gly
435 440 445

Ala Ser Ile Lys Val Ala Val Ser Ala Gly Pro Ser Ala Gly Tyr Gly
450 455 460

Ala Gly Ala Gly Ser Gly Ala Gly Ala Gly Ser Gly Ala Gly Ala Gly
465 470 475 480

Ser Gly Ala Gly Ala Gly Ser Gly Ala Gly Ala Gly Ser Gly Ala Gly
485 490 495

Ala Gly Ser Gly Ala Gly Ala Gly Ser Gly Ala Gly Ala Gly Ser Gly
500 505 510

Ala Gly Ala Gly Ser Gly Ala Ala Pro Gly Ala Ser Ile Lys Val Ala
515 520 525

Val Ser Ala Gly Pro Ser Ala Gly Tyr Gly Ala Gly Ala Gly Ser Gly
530 535 540

Ala Gly Ala Gly Ser Gly Ala Gly Ala Gly Ser Gly Ala Gly Ala Gly
545 550 555 560

Ser Gly Ala Gly Ala Gly Ser Gly Ala Gly Ala Gly Ser Gly Ala Gly
565 570 575

Ala Gly Ser Gly Ala Gly Ala Gly Ser Gly Ala Gly Ala Gly Ser Gly
580 585 590

Ala Ala Pro Gly Ala Ser Ile Lys Val Ala Val Ser Ala Gly Pro Ser
595 600 605

Ala Gly Tyr Gly Ala Gly Ala Gly Ser Gly Ala Gly Ala Gly Ser Gly
610 615 620

Ala Gly Ala Gly Ser Gly Ala Gly Ala Gly Ser Gly Ala Gly Ala Gly
625 630 635 640

Ser Gly Ala Gly Ala Gly Ser Gly Ala Gly Ala Gly Ser Gly Ala Gly
645 650 655

Ala Gly Ser Gly Ala Gly Ala Gly Ser Gly Ala Ala Pro Gly Ala Ser
660 665 670

Ile Lys Val Ala Val Ser Ala Gly Pro Ser Ala Gly Tyr Gly Ala Gly
675 680 685

Ala Gly Ser Gly Ala Gly Ala Gly Ser Gly Ala Gly Ala Gly Ser Gly
690 695 700

Ala Gly Ala Gly Ser Gly Ala Gly Ala Gly Ser Gly Ala Gly Ala Gly
705 710 715 720

Ser Gly Ala Gly Ala Gly Ser Gly Ala Gly Ala Gly Ser Gly Ala Gly
725 730 735

Ala Gly Ser Gly Ala Ala Pro Gly Ala Ser Ile Lys Val Ala Val Ser
740 745 750

Ala Gly Pro Ser Ala Gly Tyr Gly Ala Gly Ala Gly Ser Gly Ala Gly
755 760 765

Ala Gly Ser Gly Ala Gly Ala Gly Ser Gly Ala Gly Ala Gly Ser Gly
770 775 780

Ala Gly Ala Gly Ser Gly Ala Gly Ala Gly Ser Gly Ala Gly Ala Gly
785 790 795 800

Ser Gly Ala Gly Ala Gly Ser Gly Ala Gly Ala Gly Ser Gly Ala Ala
805 810 815

Pro Gly Ala Ser Ile Lys Val Ala Val Ser Ala Gly Pro Ser Ala Gly
820 825 830

Tyr Gly Ala Gly Ala Gly Ser Gly Ala Gly Ala Gly Ser Gly Ala Gly
835 840 845

Ala Gly Ser Gly Ala Gly Ala Gly Ser Gly Ala Gly Ala Gly Ser Gly
850 855 860

Ala Gly Ala Gly Ser Gly Ala Gly Ala Gly Ser Gly Ala Gly Ala Gly
865 870 875 880

Ser Gly Ala Gly Ala Gly Ser Gly Ala Ala Pro Gly Ala Ser Ile Lys
885 890 895

Val Ala Val Ser Ala Gly Pro Ser Ala Gly Tyr Gly Ala Gly Ala Gly
900 905 910

Ser Gly Ala Gly Ala Gly Ser Gly Ala Gly Ala Gly Ser Gly Ala Gly
915 920 925

Ala Gly Ser Gly Ala Gly Ala Gly Ser Gly Ala Gly Ala Gly Ser Gly
930 935 940

Ala Gly Ala Gly Ser Gly Ala Gly Ala Gly Ser Gly Ala Gly Ala Gly
945 950 955 960

Ser Gly Ala Ala Pro Gly Ala Ser Ile Lys Val Ala Val Ser Ala Gly
965 970 975

Pro Ser Ala Gly Tyr Gly Ala Gly Ala Gly Ser Gly Ala Gly Ala Gly
980 985 990

Ser Gly Ala Gly Ala Met Asp Pro Gly Arg Tyr Gln Leu Ser Ala Gly
995 1000 1005

Arg Tyr His Tyr Gln Leu Val Trp Cys Lys
1010 1015

( 2 ) INFORMATION FOR SEQ ID NO:19:

( i ) SEQUENCE CHARACTERISTICS:
( A ) LENGTH: 12 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:19:

Arg Lys Gln Ala Ala Ser Ile Lys Val Ala Val Ser
1 5 10

( 2 ) INFORMATION FOR SEQ ID NO:20:

-continued ( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:20:

```
Ile Lys Val Ala Val
1               5
```

( 2 ) INFORMATION FOR SEQ ID NO:21:

( i ) SEQUENCE CHARACTERISTICS:
( A ) LENGTH: 45 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:21:

```
Lys Lys Lys Met Gly Ala Gly Ala Gly Ser Gly Ala Gly Ala Gly Ser
1               5                   10                  15

Gly Ala Ala Val Thr Gly Arg Gly Asp Ser Pro Ala Ser Ala Ala Gly
            20                  25                  30

Tyr Gly Ala Gly Ala Gly Ser Gly Ala Gly Ala Gly Ser
        35                  40                  45
```